US007823760B2

(12) United States Patent
Zemlok et al.

(10) Patent No.: US 7,823,760 B2
(45) Date of Patent: Nov. 2, 2010

(54) POWERED SURGICAL STAPLING DEVICE PLATFORM

(75) Inventors: Michael Zemlok, Prospect, CT (US); David C. Racenet, Litchfield, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/799,766

(22) Filed: May 1, 2007

(65) Prior Publication Data

US 2008/0272172 A1 Nov. 6, 2008

(51) Int. Cl.
*A61B 17/10* (2006.01)

(52) U.S. Cl. .............. 227/175.1; 227/175.2; 227/182.1; 227/175.3; 227/19

(58) Field of Classification Search .............. 227/175.1, 227/19, 175.2, 175.3, 182.1
See application file for complete search history.

(56) References Cited

U.S. PATENT DOCUMENTS

| | | | |
|---|---|---|---|
| 37,165 | A | 12/1862 | Gary |
| 3,079,606 | A | 3/1963 | Bobrov et al. |
| 3,209,754 | A | 10/1965 | Brown |
| 3,273,562 | A | 9/1966 | Brown |
| 3,490,675 | A | 1/1970 | Green et al. |
| 3,499,591 | A | 3/1970 | Green |
| 3,528,693 | A | 9/1970 | Pearson et al. |
| 3,744,495 | A | 7/1973 | Johnson |
| 3,949,924 | A | 4/1976 | Green |
| 4,060,089 | A | 11/1977 | Noiles |
| 4,204,623 | A | 5/1980 | Green |
| 4,217,902 | A | 8/1980 | March |
| 4,263,903 | A | 4/1981 | Griggs |
| 4,275,813 | A | 6/1981 | Noiles |
| 4,331,277 | A | 5/1982 | Green |
| 4,428,376 | A | 1/1984 | Mericle |
| 4,429,695 | A | 2/1984 | Green |

(Continued)

FOREIGN PATENT DOCUMENTS

| | | |
|---|---|---|
| EP | 0 537 570 B1 | 4/1993 |

(Continued)

OTHER PUBLICATIONS

European Search Report dated Apr. 17, 2007 for Corresponding Patent Application EP06026840.

(Continued)

*Primary Examiner*—Rinaldi I. Rada
*Assistant Examiner*—Michelle Lopez

(57) ABSTRACT

The present disclosure provides for a surgical instrument which includes a housing and an endoscopic portion extending distally from the housing and defining a first longitudinal axis. The surgical instrument also includes an end effector disposed adjacent a distal portion of the endoscopic portion. The end effector includes an anvil assembly and a cartridge assembly. The anvil assembly is pivotally coupled to the cartridge assembly to be movable from a first actuation position to at least one other second actuation position. The surgical instrument further includes a firing rod having a shaft defining a second longitudinal axis, the shaft having a cam member which is in mechanical cooperation with the anvil assembly and is configured to move the anvil assembly from the first actuation position to the at least one other second actuation position upon rotation of the firing rod about the second longitudinal axis.

19 Claims, 15 Drawing Sheets

160 302 408 402 406 300 332

160 302 402 406 300 332 408

U.S. PATENT DOCUMENTS 4,454,875 A 6/1984 Pratt et al.
4,485,816 A 12/1984 Krumme
4,485,817 A 12/1984 Swiggett
4,488,523 A 12/1984 Shichman
4,508,253 A 4/1985 Green
4,508,523 A 4/1985 Leu
4,522,206 A 6/1985 Whipple et al.
4,534,350 A 8/1985 Goldman et al.
4,566,620 A 1/1986 Green et al.
4,570,623 A 2/1986 Ellison et al.
4,606,343 A 8/1986 Conta et al.
4,606,344 A 8/1986 Di Giovanni
4,610,383 A 9/1986 Rothfuss et al.
4,612,923 A 9/1986 Kronenthal
4,612,933 A 9/1986 Brinkerhoff et al.
D286,442 S 10/1986 Korthoff et al.
4,627,437 A 12/1986 Bedi et al.
4,635,637 A 1/1987 Schreiber
4,662,371 A 5/1987 Whipple et al.
4,671,280 A 6/1987 Dorband et al.
4,705,038 A 11/1987 Sjostrom et al.
4,712,550 A 12/1987 Sinnett
4,719,917 A 1/1988 Barrows et al.
4,724,839 A 2/1988 Bedi
4,805,617 A 2/1989 Bedi et al.
4,807,628 A 2/1989 Peters et al.
4,960,420 A 10/1990 Goble et al.
4,962,877 A 10/1990 Hervas
4,990,153 A 2/1991 Richards
4,994,073 A 2/1991 Green
4,995,877 A 2/1991 Ams et al.
5,040,715 A 8/1991 Green et al.
5,065,929 A 11/1991 Schulze et al.
5,089,009 A 2/1992 Green
5,108,422 A 4/1992 Green et al.
5,114,399 A 5/1992 Kovalcheck
5,129,570 A 7/1992 Schulze et al.
5,143,453 A 9/1992 Girnes
5,203,864 A 4/1993 Phillips
5,207,697 A 5/1993 Carusillo et al.
5,209,756 A 5/1993 Seedhom et al.
5,258,008 A 11/1993 Wilk
5,271,543 A 12/1993 Grant et al.
RE34,519 E 1/1994 Fox et al.
5,282,829 A 2/1994 Hermes
5,300,081 A 4/1994 Young et al.
5,307,976 A 5/1994 Olson et al.
5,312,023 A 5/1994 Green et al.
5,312,024 A 5/1994 Grant et al.
5,313,935 A 5/1994 Green et al.
5,318,221 A 6/1994 Green et al.
5,326,013 A 7/1994 Green et al.
5,330,486 A 7/1994 Wilk
5,332,142 A 7/1994 Robinson et al.
5,342,376 A 8/1994 Ruff
5,350,355 A 9/1994 Sklar
5,356,064 A 10/1994 Green et al.
5,359,993 A 11/1994 Slater et al.
5,364,001 A 11/1994 Bryan
5,381,943 A 1/1995 Allen et al.
5,383,874 A 1/1995 Jackson et al.
5,383,880 A 1/1995 Hooven
5,389,098 A 2/1995 Tsuruta et al.
5,395,030 A 3/1995 Kuramoto et al.
5,395,033 A 3/1995 Byrne et al.
5,403,312 A 4/1995 Yates et al.
5,405,344 A 4/1995 Williamson et al.
5,411,508 A 5/1995 Bessler et al.
5,413,267 A 5/1995 Solyntjes et al.
5,431,323 A 7/1995 Smith et al.
5,464,144 A 11/1995 Guy et al.
5,467,911 A 11/1995 Tsuruta et al.
5,478,344 A 12/1995 Stone et al.
5,482,100 A 1/1996 Kuhar
5,485,947 A 1/1996 Olson et al.
5,485,952 A * 1/1996 Fontayne ................. 227/178.1
5,487,499 A 1/1996 Sorrentino et al.
5,497,933 A 3/1996 DeFonzo et al.
5,500,000 A 3/1996 Feagin et al.
5,503,320 A 4/1996 Webster et al.
5,507,743 A 4/1996 Edwards et al.
5,518,163 A 5/1996 Hooven
5,518,164 A 5/1996 Hooven
5,526,822 A 6/1996 Burbank et al.
5,529,235 A 6/1996 Boiarski et al.
5,531,744 A 7/1996 Nardella et al.
5,533,661 A 7/1996 Main et al.
5,535,934 A 7/1996 Boiarski et al.
5,535,937 A 7/1996 Boiarski et al.
5,558,671 A 9/1996 Yates
5,560,532 A 10/1996 DeFonzo et al.
5,562,239 A 10/1996 Boiarski et al.
5,575,799 A 11/1996 Bolanos et al.
5,582,611 A 12/1996 Tsuruta et al.
5,584,835 A 12/1996 Greenfield
5,601,224 A 2/1997 Bishop et al.
5,601,558 A 2/1997 Torrie et al.
5,607,095 A 3/1997 Smith et al.
5,609,285 A 3/1997 Grant et al.
5,609,560 A 3/1997 Ichikawa et al.
5,624,452 A 4/1997 Yates
5,632,433 A 5/1997 Grant et al.
5,642,848 A 7/1997 Ludwig et al.
5,653,374 A 8/1997 Young et al.
5,658,300 A 8/1997 Bito et al.
5,658,312 A 8/1997 Green et al.
5,662,662 A * 9/1997 Bishop et al. ............... 606/143
5,665,085 A 9/1997 Nardella
5,667,513 A 9/1997 Torrie et al.
5,667,517 A * 9/1997 Hooven ...................... 606/151
5,667,527 A 9/1997 Cook
5,669,544 A 9/1997 Schulze et al.
5,673,841 A 10/1997 Schulze et al.
5,676,674 A 10/1997 Bolanos et al.
5,680,981 A 10/1997 Mililli et al.
5,680,982 A * 10/1997 Schulze et al. ........... 227/175.1
5,692,668 A 12/1997 Schulze et al.
5,695,524 A 12/1997 Kelley et al.
5,702,447 A 12/1997 Walch et al.
5,704,534 A * 1/1998 Huitema et al. .......... 227/175.1
5,713,505 A 2/1998 Huitema
5,713,896 A 2/1998 Nardella
5,715,987 A 2/1998 Kelley et al.
5,716,366 A 2/1998 Yates
5,720,753 A 2/1998 Sander et al.
5,725,529 A 3/1998 Nicholson et al.
5,728,110 A * 3/1998 Vidal et al. ................. 606/143
5,728,116 A 3/1998 Rosenman
5,730,757 A 3/1998 Benetti et al.
5,735,848 A 4/1998 Yates et al.
5,738,474 A 4/1998 Blewett
5,755,726 A 5/1998 Pratt
5,759,171 A 6/1998 Coelho et al.
5,769,303 A * 6/1998 Knodel et al. ............ 227/176.1
5,779,130 A 7/1998 Alesi et al.
5,782,397 A 7/1998 Koukline
5,788,698 A 8/1998 Savornin
5,810,811 A 9/1998 Yates et al.
5,823,066 A 10/1998 Huitema et al.
5,829,662 A 11/1998 Allen et al.
5,830,121 A 11/1998 Enomoto et al.
5,849,023 A 12/1998 Mericle
5,849,028 A 12/1998 Chen
5,855,311 A 1/1999 Hamblin et al.

5,861,005 A 1/1999 Kontos
5,865,361 A 2/1999 Milliman et al.
5,876,401 A 3/1999 Schulze et al.
5,891,156 A 4/1999 Gessner et al.
5,893,813 A 4/1999 Yamamoto
5,895,396 A 4/1999 Day et al.
5,897,562 A 4/1999 Bolanos et al.
5,906,607 A 5/1999 Taylor et al.
5,911,721 A 6/1999 Nicholson et al.
5,918,791 A 7/1999 Sorrentino et al.
5,928,222 A 7/1999 Kleinerman
5,944,717 A 8/1999 Lee et al.
5,944,736 A 8/1999 Taylor et al.
5,954,259 A * 9/1999 Viola et al. .............. 227/176.1
5,961,521 A 10/1999 Roger
5,964,394 A 10/1999 Robertson
5,968,044 A 10/1999 Nicholson et al.
5,976,171 A 11/1999 Taylor
5,980,518 A 11/1999 Carr et al.
5,980,548 A 11/1999 Evans et al.
5,991,355 A 11/1999 Dahlke
5,991,650 A 11/1999 Swanson et al.
5,992,724 A 11/1999 Snyder
5,997,552 A 12/1999 Person et al.
6,004,335 A 12/1999 Vaitekunas et al.
6,007,550 A 12/1999 Wang et al.
6,010,054 A 1/2000 Johnson et al.
6,013,077 A 1/2000 Harwin
6,015,417 A 1/2000 Reynolds, Jr.
6,017,354 A 1/2000 Culp et al.
6,030,410 A 2/2000 Zurbrugg
6,032,849 A 3/2000 Mastri et al.
6,039,731 A 3/2000 Taylor et al.
6,063,078 A 5/2000 Wittkampf
6,063,095 A 5/2000 Wang et al.
6,077,246 A 6/2000 Kullas et al.
6,079,606 A 6/2000 Milliman et al.
6,080,150 A 6/2000 Gough
6,083,242 A 7/2000 Cook
6,090,123 A 7/2000 Culp et al.
6,092,422 A 7/2000 Binnig et al.
6,109,500 A 8/2000 Alli et al.
6,113,592 A 9/2000 Taylor
6,123,702 A 9/2000 Swanson et al.
H1904 H 10/2000 Yates et al.
6,126,058 A 10/2000 Adams et al.
6,126,651 A 10/2000 Mayer
6,127,811 A 10/2000 Shenoy et al.
6,132,425 A 10/2000 Gough
6,165,169 A 12/2000 Panescu et al.
6,166,538 A 12/2000 D'Alfonso
6,179,840 B1 1/2001 Bowman
6,187,009 B1 2/2001 Herzog et al.
6,187,019 B1 2/2001 Stefanchik et al.
6,190,401 B1 2/2001 Green et al.
6,193,501 B1 2/2001 Masel et al.
6,202,914 B1 3/2001 Geiste et al.
6,217,573 B1 4/2001 Webster
6,228,534 B1 5/2001 Takeuchi et al.
6,231,565 B1 5/2001 Tovey et al.
6,236,874 B1 5/2001 Devlin et al.
6,237,604 B1 5/2001 Burnside et al.
6,241,139 B1 6/2001 Milliman et al.
6,245,065 B1 6/2001 Panescu et al.
6,248,117 B1 6/2001 Blatter
6,250,532 B1 6/2001 Green et al.
6,258,111 B1 7/2001 Ross et al.
6,264,086 B1 7/2001 McGuckin, Jr.
6,264,087 B1 7/2001 Whitman
6,264,653 B1 7/2001 Falwell
6,281,471 B1 8/2001 Smart
6,288,534 B1 9/2001 Starkweather et al.
6,290,701 B1 9/2001 Enayati
6,293,943 B1 9/2001 Panescu et al.
6,295,330 B1 9/2001 Skog et al.
6,315,184 B1 11/2001 Whitman
6,329,778 B1 12/2001 Culp et al.
6,330,965 B1 12/2001 Milliman et al.
6,346,104 B2 2/2002 Daly et al.
6,355,066 B1 3/2002 Kim
6,364,884 B1 4/2002 Bowman et al.
6,387,092 B1 5/2002 Burnside et al.
6,388,240 B2 5/2002 Schulz et al.
6,402,766 B2 6/2002 Bowman et al.
H2037 H 7/2002 Yates et al.
6,412,279 B1 7/2002 Coleman et al.
6,425,903 B1 7/2002 Voegele
6,436,097 B1 8/2002 Nardella
6,436,107 B1 8/2002 Wang et al.
6,436,110 B2 8/2002 Bowman et al.
6,443,973 B1 9/2002 Whitman
6,447,517 B1 9/2002 Bowman
6,461,372 B1 10/2002 Jensen et al.
6,478,210 B2 11/2002 Adams et al.
6,497,707 B1 12/2002 Bowman et al.
6,505,768 B2 1/2003 Whitman
6,515,273 B2 2/2003 Al-Ali
6,517,565 B1 2/2003 Whitman et al.
6,524,316 B1 2/2003 Nicholson et al.
6,533,157 B1 3/2003 Whitman
6,540,751 B2 4/2003 Enayati
6,544,273 B1 4/2003 Harari et al.
6,554,852 B1 4/2003 Oberlander
6,562,071 B2 5/2003 Jarvinen
6,578,579 B2 6/2003 Burnside et al.
6,601,748 B1 8/2003 Fung et al.
6,601,749 B2 8/2003 Sullivan et al.
6,602,252 B2 8/2003 Mollenauer
6,611,793 B1 8/2003 Burnside et al.
6,616,821 B2 9/2003 Broadley et al.
6,629,986 B1 10/2003 Ross et al.
6,651,669 B1 11/2003 Burnside
6,656,177 B2 12/2003 Truckai et al.
6,669,073 B2 12/2003 Milliman et al.
6,669,705 B2 12/2003 Westhaver et al.
6,696,008 B2 2/2004 Brandinger
6,698,643 B2 3/2004 Whitman
6,699,177 B1 3/2004 Wang et al.
6,716,233 B1 4/2004 Whitman
6,736,085 B1 5/2004 Esnouf
6,792,390 B1 9/2004 Burnside et al.
6,817,508 B1 11/2004 Racenet et al.
6,830,174 B2 12/2004 Hillstead et al.
6,843,403 B2 1/2005 Whitman
6,846,307 B2 1/2005 Whitman et al.
6,846,308 B2 1/2005 Whitman et al.
6,846,309 B2 1/2005 Whitman et al.
6,849,071 B2 2/2005 Whitman et al.
6,861,639 B2 3/2005 Al-Ali
6,872,214 B2 3/2005 Sonnenschein et al.
6,899,538 B2 5/2005 Matoba
6,900,004 B2 5/2005 Satake
6,905,057 B2 6/2005 Swayze et al.
6,926,636 B2 8/2005 Luper
6,953,139 B2 10/2005 Milliman et al.
6,959,852 B2 11/2005 Shelton et al.
6,979,328 B2 12/2005 Baerveldt et al.
6,981,628 B2 1/2006 Wales
6,981,941 B2 1/2006 Whitman et al.
6,988,649 B2 1/2006 Shelton et al.
7,000,819 B2 2/2006 Swayze et al.
7,032,798 B2 4/2006 Whitman et al.
7,044,353 B2 5/2006 Mastri et al.
7,048,687 B1 5/2006 Reuss et al.
7,059,508 B2 6/2006 Shelton et al.
7,077,856 B2 7/2006 Whitman 7,083,075 B2 8/2006 Swayze et al.
7,097,089 B2 8/2006 Marczyk
7,111,769 B2 9/2006 Wales et al.
7,118,564 B2 10/2006 Ritchie et al.
7,122,029 B2 10/2006 Koop et al.
7,128,253 B2 10/2006 Mastri et al.
7,128,254 B2 10/2006 Shelton et al.
7,140,528 B2 11/2006 Shelton, IV
7,143,924 B2 12/2006 Scirica et al.
7,143,925 B2 12/2006 Shelton, IV et al.
7,143,926 B2 12/2006 Shelton, IV
7,147,138 B2 12/2006 Shelton, IV
7,186,966 B2 3/2007 Al-Ali
7,193,519 B2 3/2007 Root et al.
7,217,269 B2 5/2007 El-Galley et al.
7,220,232 B2 5/2007 Suorsa et al.
7,240,817 B2 7/2007 Higuchi
7,241,270 B2 7/2007 Jorzewski et al.
7,246,734 B2 7/2007 Shelton, IV
7,303,108 B2 12/2007 Shelton, IV
7,328,828 B2 2/2008 Ortiz et al.
7,335,169 B2 2/2008 Thompson et al.
7,364,061 B2 4/2008 Swayze et al.
7,380,695 B2 6/2008 Doll et al.
7,380,696 B2 6/2008 Shelton, IV et al.
7,404,508 B2 7/2008 Smirh et al.
7,422,136 B1 9/2008 Marczyk
2002/0025891 A1 2/2002 Colosky et al.
2002/0111641 A1 8/2002 Peterson et al.
2002/0165541 A1 11/2002 Whitman
2003/0009195 A1 1/2003 Field et al.
2003/0073981 A1 4/2003 Whitman et al.
2003/0114851 A1 6/2003 Truckai et al.
2003/0120306 A1 6/2003 Burbank et al.
2004/0094597 A1 5/2004 Whitman et al.
2004/0232199 A1 11/2004 Shelton, IV et al.
2004/0232201 A1 11/2004 Wenchell et al.
2005/0006429 A1 1/2005 Wales et al.
2005/0006430 A1 1/2005 Wales
2005/0006431 A1 1/2005 Shelton, IV et al.
2005/0006434 A1 1/2005 Wales et al.
2005/0010236 A1 1/2005 Frister
2005/0023324 A1 2/2005 Doll et al.
2005/0067458 A1 3/2005 Swayze et al.
2005/0070925 A1 3/2005 Shelton, IV et al.
2005/0070958 A1 3/2005 Swayze et al.
2005/0072827 A1 4/2005 Mollenauer
2005/0131390 A1 6/2005 Heinrich et al.
2005/0139636 A1 6/2005 Schwemberger et al.
2005/0145674 A1 7/2005 Sonnenschein et al.
2005/0178813 A1 8/2005 Swayze et al.
2005/0187576 A1 8/2005 Whitman et al.
2005/0192609 A1 9/2005 Whitman et al.
2005/0228341 A1 10/2005 Edgerley
2005/0247753 A1 11/2005 Kelly et al.
2006/0000867 A1 1/2006 Shelton, IV et al.
2006/0022014 A1 2/2006 Shelton, IV
2006/0022015 A1 2/2006 Shelton, IV
2006/0049229 A1 3/2006 Milliman et al.
2006/0097025 A1 5/2006 Milliman et al.
2006/0151567 A1 7/2006 Roy
2006/0175375 A1 8/2006 Shelton, IV
2007/0023476 A1 2/2007 Whitman et al.
2007/0023477 A1 2/2007 Whitman et al.
2007/0029363 A1 2/2007 Popov
2007/0029364 A1 2/2007 Kruszynski et al.
2007/0039995 A1 2/2007 Schwemberger et al.
2007/0039996 A1 2/2007 Mather et al.
2007/0039997 A1 2/2007 Mather et al.
2007/0084896 A1 4/2007 Doll et al.
2007/0084897 A1 4/2007 Shelton, IV et al.
2007/0102472 A1 5/2007 Shelton, IV
2007/0102473 A1 5/2007 Shelton, IV et al.
2007/0102474 A1 5/2007 Shelton, IV et al.
2007/0102475 A1 5/2007 Ortiz et al.
2007/0125826 A1 6/2007 Shelton, IV
2007/0152014 A1 7/2007 Gillum et al.
2007/0158385 A1 7/2007 Hueil et al.
2007/0175947 A1* 8/2007 Ortiz et al. ............... 227/175.1
2007/0175949 A1 8/2007 Shelton, IV et al.
2007/0175950 A1 8/2007 Shelton, IV et al.
2007/0175951 A1 8/2007 Shelton, IV et al.
2007/0175952 A1 8/2007 Shelton, IV
2007/0175953 A1 8/2007 Shelton, IV
2007/0175955 A1 8/2007 Shelton, IV et al.
2007/0175956 A1 8/2007 Swayze et al.
2007/0175957 A1 8/2007 Shelton, IV
2007/0175958 A1 8/2007 Shelton, IV
2007/0175959 A1 8/2007 Shelton, IV
2007/0175960 A1 8/2007 Shelton, IV et al.
2007/0175961 A1 8/2007 Shelton, IV et al.
2007/0175962 A1 8/2007 Shelton, IV et al.
2007/0175964 A1 8/2007 Shelton, IV et al.
2007/0187453 A1 8/2007 Smith et al.
2007/0219563 A1 9/2007 Voegele
2007/0265640 A1* 11/2007 Kortenbach et al. ......... 606/139
2007/0278277 A1 12/2007 Wixey et al.
2008/0029570 A1 2/2008 Shelton et al.
2008/0029571 A1 2/2008 Shelton et al.
2008/0029572 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0029576 A1 2/2008 Shelton et al.
2008/0029577 A1 2/2008 Shelton et al.
2008/0048002 A1 2/2008 Shelton et al.
2008/0110957 A1 5/2008 McBride et al.
2008/0135600 A1 6/2008 Hiranuma et al.
2008/0164296 A1 7/2008 Shelton et al.
2008/0169329 A1 7/2008 Shelton et al.
2008/0185419 A1 8/2008 Smith et al.

FOREIGN PATENT DOCUMENTS

EP 0 647 431 A2 4/1995
EP 0 738 501 A1 10/1996
WO WO 97/29694 8/1997
WO WO 97/40760 A1 11/1997
WO WO 99/52489 A1 10/1999
WO WO 03/026511 4/2003
WO WO 03/030743 A2 4/2003
WO WO 2004/032760 A2 4/2004
WO WO 2007/030753 A2 3/2007
WO WO 2007/118179 A2 10/2007

OTHER PUBLICATIONS

International Search Report for corresponding PCT Application—PCT/US06/21524—Date of Mailing May 28, 2008 (4 Pages).

Detemple, P., "Microtechnology in Modern Health Care", *Med Device Technol*. 9(9):18-25 (1998).

European Search Report for corresponding EP 08252703 dated Oct. 31, 2008 (3 pages).

European Search Report for corresponding EP 08252703.7 dated Oct. 31, 2008 (7 pages).

European Search Report for Corresponding EP 08251357 date of mailing is Sep. 29, 2009 (3 pages).

* cited by examiner

401
C
220
212
224
216
200
210
202
204
360
100
C

POWERED SURGICAL STAPLING DEVICE PLATFORM

BACKGROUND

1. Technical Field

The present disclosure relates to surgical instruments for fastening body tissue and, more particularly, to a powered surgical instrument having a firing rod configured to be movable and rotatable to affect rotation, articulation and actuation of portions of the instrument.

2. Background of Related Art

Surgical devices wherein tissue is grasped or clamped between opposing jaw structure and then joined by surgical fasteners are well known in the art. In some instruments, a knife is provided to cut the tissue which has been joined by the fasteners. The fasteners are typically in the form of surgical staples but two-part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. Several instruments include clamps, handles and/or knobs to affect actuation along with rotation and articulation of an end effector. Generally, the stapling operation is effected by cam bars that travel longitudinally through the staple cartridge, with the cam bars acting upon staple pushers to sequentially eject the staples from the staple cartridge. Such stapling devices can be used in open as well as endoscopic and/or laparoscopic surgical procedures.

It would be extremely beneficial to provide a powered surgical device for use during surgical procedures that can utilize a new and improved mechanism for articulating and/or actuating the tool tip to automate the stapling process.

SUMMARY

According to one aspect of the present disclosure, a surgical instrument is provided. The surgical instrument includes a housing and an endoscopic portion extending distally from the housing and defining a first longitudinal axis. The surgical instrument also includes an end effector disposed adjacent a distal portion of the endoscopic portion. The end effector may include an anvil assembly and a cartridge assembly. The anvil assembly is pivotally coupled to the cartridge assembly to be movable from a first actuation position to at least one other second actuation position. The surgical instrument further includes a firing rod having a shaft defining a second longitudinal axis, the shaft having a cam member which is in mechanical cooperation with the anvil assembly and is configured to move the anvil assembly from the first actuation position to the at least one other second actuation position upon rotation of the firing rod about the second longitudinal axis.

According to another aspect of the present disclosure a surgical instrument is provided with a housing and an endoscopic portion extending distally from the housing and defining a first longitudinal axis. The surgical instrument also includes an end effector disposed adjacent a distal portion of the endoscopic portion. The end effector includes a first jaw member and a second jaw member, the second jaw member is pivotally coupled to the first jaw member to be movable from a first actuation position to at least one other second actuation position. The surgical instrument further includes a firing rod including a shaft defining a second longitudinal axis. The shaft has a cam member which is in mechanical cooperation with the second jaw member and is configured to move the second jaw member from the first actuation position to the at least one other second actuation position upon rotation of the firing rod about the second longitudinal axis.

According to a further embodiment of the present disclosure, a tool assembly is provided. The tool assembly includes an end effector disposed adjacent a distal endoscopic portion. The end effector includes an anvil assembly and a cartridge assembly. The anvil assembly is pivotally coupled to the cartridge assembly to be movable from a first actuation position to at least one other second actuation position. The tool assembly also includes a firing rod including a shaft defining a second longitudinal axis. The shaft has a cam member which is in mechanical cooperation with the anvil assembly and is configured to move the anvil assembly from the first actuation position to the at least one other second actuation position upon rotation of the firing rod about the second longitudinal axis.

According to another aspect of the present disclosure, a surgical instrument is disclosed, which includes a housing, an endoscopic portion extending distally from the housing and an intermediate shaft having a proximal end configured for connection to a distal end of the endoscopic portion, the intermediate shaft being flexible. The instrument also includes a loading unit having an end effector for performing a surgical function. The loading unit includes a proximal portion configured for connection to a distal end of the intermediate shaft.

According to a further aspect of the present disclosure, a surgical instrument including a housing and an endoscopic portion extending distally from the housing is disclosed. The housing includes at least a first angled tube and a second angle tube, the first angled tube and second angled tube being rotatably movable with respect to one another between a plurality of positions including a first position defining a substantially straight shaft and a second, fully articulated position and an end effector disposed adjacent a distal portion of the endoscopic portion.

DESCRIPTION OF THE DRAWINGS

An embodiment of the presently disclosed powered surgical instrument is disclosed herein with reference to the drawings, wherein.

DETAILED DESCRIPTION OF EMBODIMENTS

Figure 1:
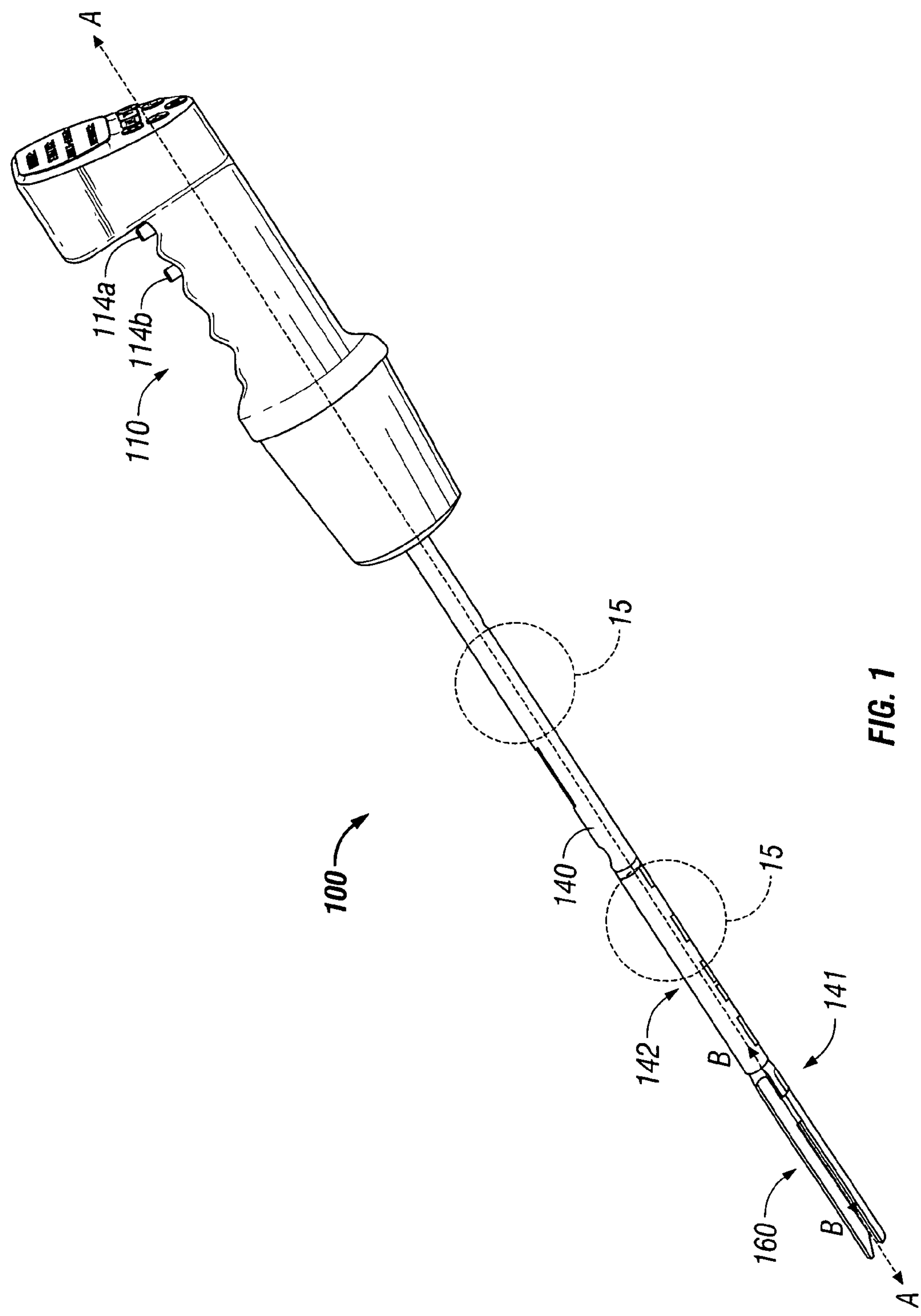
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 100. Referring initially to FIG. 1, powered surgical instrument 100 includes a housing 110, an endoscopic portion 140 defining a longitudinal axis A-A extending therethrough, and an end effector 160, defining a longitudinal axis B-B (illustrated substantially aligned with axis A-A in FIG. 1) extending therethrough. Endoscopic portion 140 extends distally from housing 110 and end effector 160 is disposed adjacent a distal portion 142 of endoscopic portion 140.

It is envisioned that end effector 160 is reusable and is configured to accept a staple cartridge and/or is part of a disposable loading unit. Further details of a disposable loading unit are described in detail in commonly-owned U.S. Pat. No. 6,241,139 to Miliman, the entire contents of which are hereby incorporated by reference herein.

The end effector 160 is coupled to the endoscopic portion 140 via a mounting assembly 141. The end effector 160 may be any end effector used in linear stapling devices, such as ENDO GIA™, GIA™, TA™, ENDO TA™, EEA™ staplers sold by U.S. Surgical Corp, of Norwalk, Conn. Such end effectors may be coupled to endoscopic portion 140 of powered surgical instrument 100. Mounting assembly 141 is pivotally secured to the distal portion 142 and is fixedly secured to a proximal end of tool assembly 160. This allows for pivotal movement of mounting assembly 141 about an axis perpendicular to the longitudinal axis A-A. Pivotal movement occurs between a non-articulated position in which the longitudinal axis of tool assembly 160 is aligned with the longitudinal axis A-A and an articulated position in which the longitudinal axis B-B of the tool assembly 160 is disposed at an angle to the longitudinal axis A-A of endoscopic portion 140.

Figure 2:
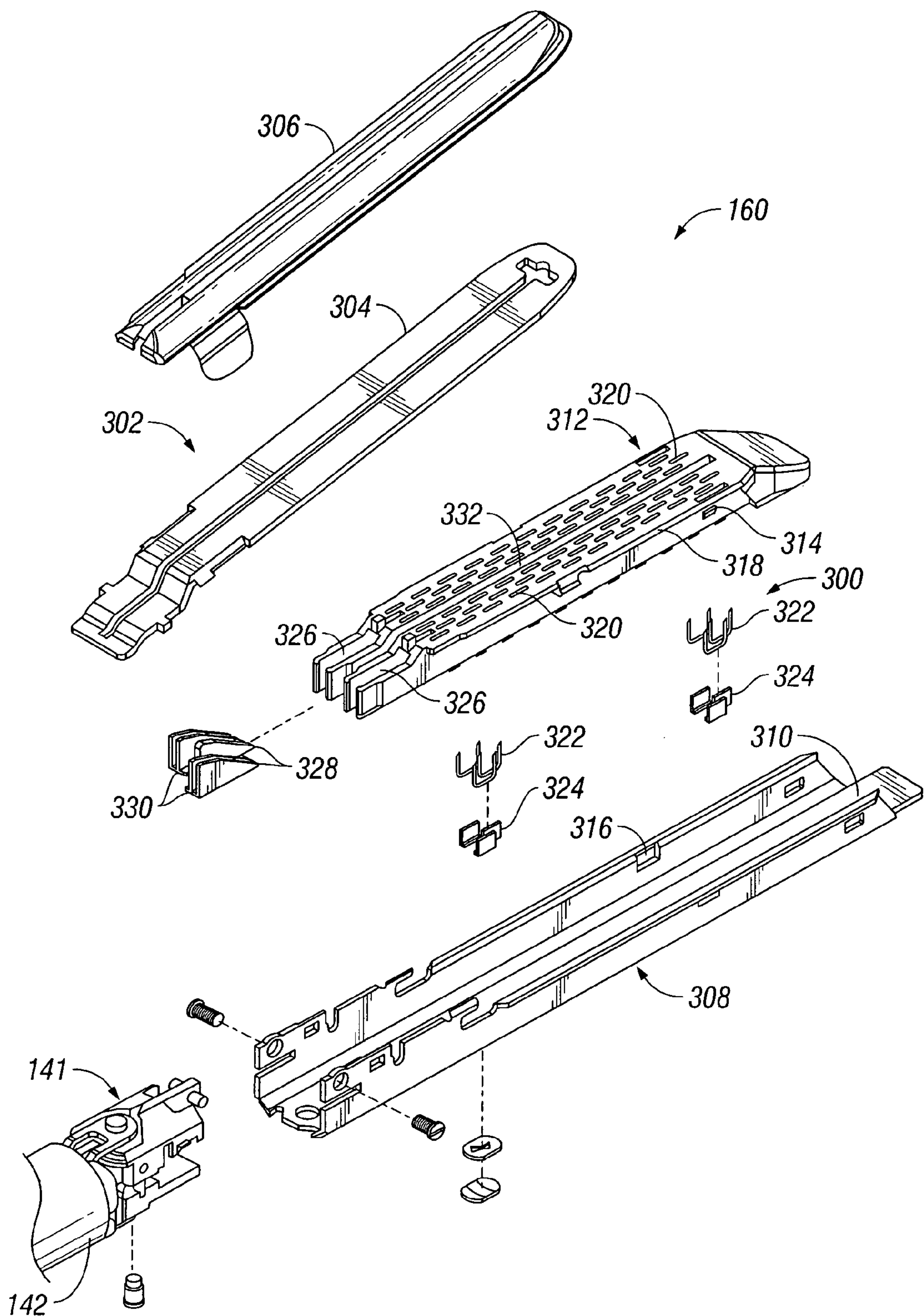
FIG. 2 is an exploded view of the staple cartridge and anvil or business head of the surgical instrument shown in FIG. 1.
Figure 3:
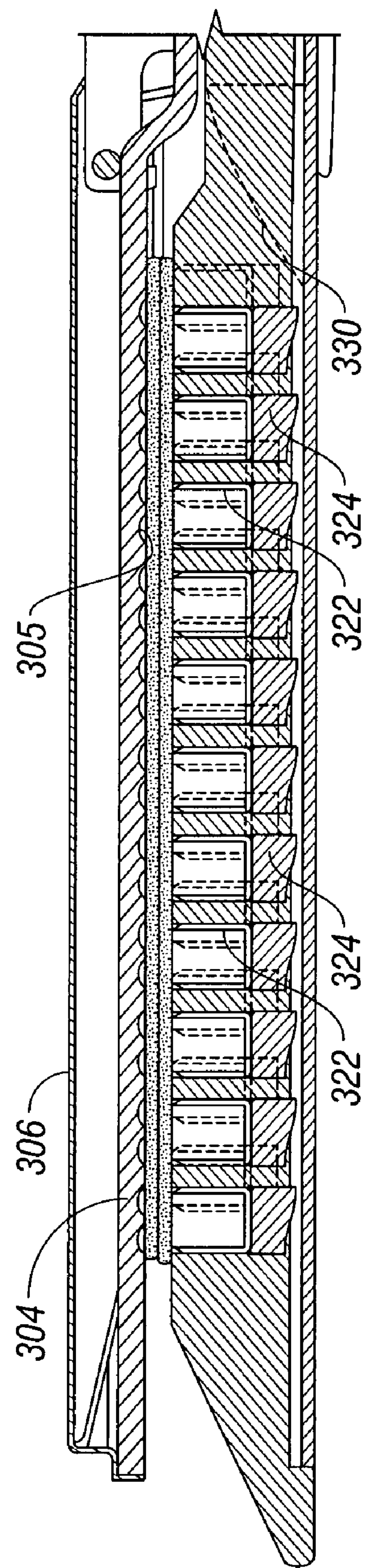
FIG. 3 is a side cross-sectional view of the staple cartridge and anvil or business head of the surgical instrument shown in FIG. 1.

Referring to FIGS. 2 and 3, tool assembly 160 includes a cartridge assembly 300 (e.g., first jaw of the tool assembly) and an anvil assembly 302 (e.g., second of the tool assembly). Anvil assembly 302 includes an anvil portion 304 having a plurality of staple deforming concavities 305 (FIG. 3) and a cover plate 306 secured to a top surface of anvil portion 304. Cartridge assembly 300 includes carrier 308 which defines an elongated support channel 310 which is dimensioned and configured to receive staple cartridge 312. Corresponding tabs 314 and slots 316 formed along staple cartridge 312 and elongated support channel 310, respectively, function to retain staple cartridge 312 at a fixed location within support channel 310. A pair of support struts 318 formed on staple cartridge 312 is positioned to rest on side walls of carrier 308 to further stabilize staple cartridge 312 within support channel 310.

Staple cartridge 312 includes retention slots 320 for receiving a plurality of staples or fasteners 322 and pushers 324. A plurality of laterally spaced apart longitudinal slots 326 extends through staple cartridge 312 to accommodate upstanding cam wedges 328 of an actuation sled 330. A central longitudinal slot 332 extends along substantially the length of staple cartridge 312 to facilitate passage of a knife blade (not explicitly shown).

Figure 4A:
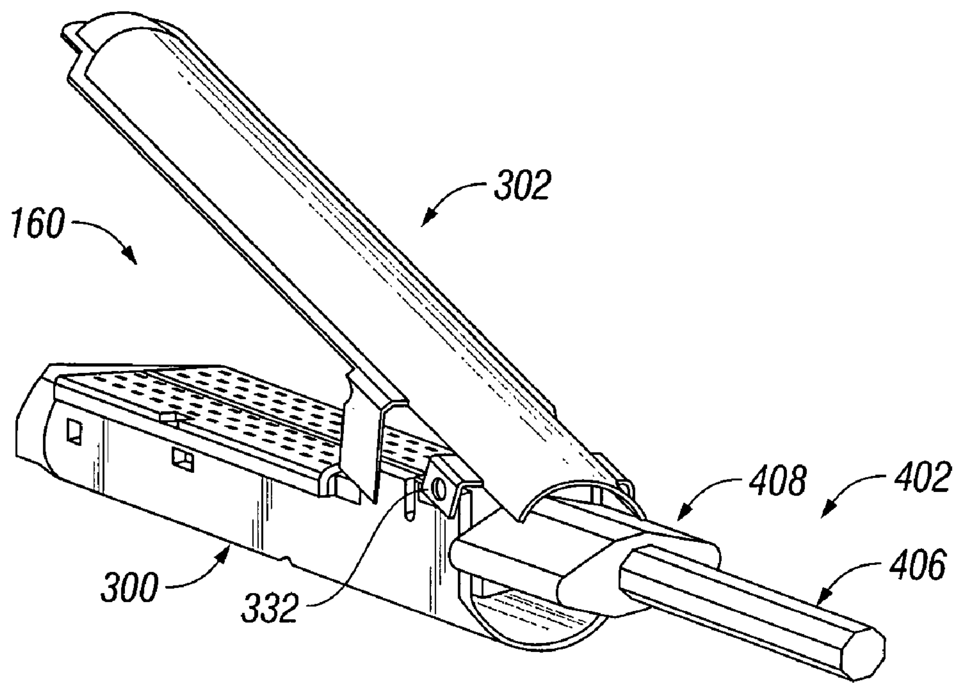
FIGS. 4A-B are perspective views of a shaped firing rod and cammed clamping of the stapler anvil in the open and closed positions.
Figure 4B:
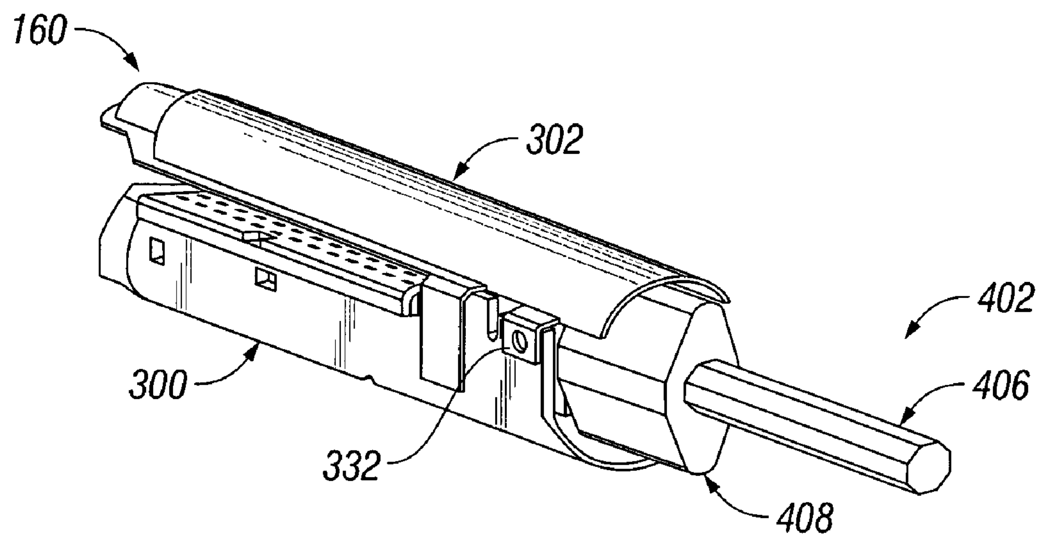
Figure 5:
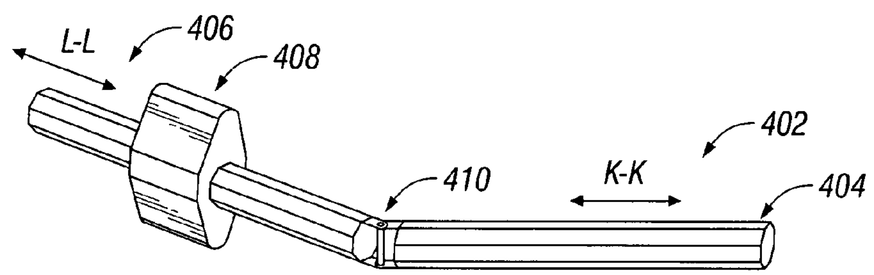
FIG. 5 is a perspective view of the cam and the shaped firing rod of the surgical instrument of FIG. 1.

FIGS. 4A-B and 5 show a firing rod 402 for articulation and actuation of the tool assembly 160. The firing rod 402 includes a proximal shaft 404 which extends the length of the endoscopic portion 140 and the distal portion 142 and a distal shaft 406 which is disposed within the tool assembly 160. The proximal shaft 404 and the distal shaft 406 are pivotally linked via a pivot member 410 which passes through bores (not explicitly shown) within the distal end of the proximal shaft 404 and the proximal end of the distal shaft 406. Pivotal movement occurs between a non-articulated position in which the longitudinal axis of distal shaft 406 is aligned with the longitudinal axis K-K and an articulated position in which the longitudinal axis L-L of the tool distal shaft 406 is disposed at an angle to the longitudinal axis K-K of proximal shaft 404. The firing rod 402 may be formed from a rigid and/or flexible material. Forming the firing rod 402 from a flexible material obviates the need for pivot member 410 as the proximal shaft 404 can pivot with respect to the distal shaft 406 by nature of the flexibility of the material. It is envisioned that other pivoting mechanisms may be used, such as plastic or rubber bands interconnecting the proximal and distal portions 404 and 406.

The proximal shaft 404 and the distal shaft 406 of the firing rod 402 incorporate a plurality of surface features or shapes along the length thereof. In embodiments, the firing rod 402 has a generally cylindrical structure with a non-circular cross-section (e.g., hexagonal, octagonal, star-shaped, oval, etc.) It is also envisioned the firing rod 402 may include one or more curved shapes (e.g., helix, screw, etc.) These structures allow for gripping of the firing rod 402 and rotation thereof to actuate the tool assembly 160.

The firing rod 402 is disposed within a passage (not explicitly shown) of the endoscopic portion 140 and the distal portion 142, the passage has the same cross-sectional profile as the firing rod 402 such that the firing rod 402 is in mechanical cooperation with the passage but can simultaneously freely slide therein. This is especially useful if the firing rod 402 is formed from a flexible material since this prevents deformation of the firing rod 402 within the passage.

The firing rod 402 is configured for opening and closing of the anvil assembly 302 as well as pushing actuation sled 330 through longitudinal slots 326 of staple cartridge 312 to advance cam wedges 328 into sequential contact with pushers 324 to staple tissue. The firing rod 402 is configured to be selectively moved between a plurality of positions. In certain embodiments, the firing rod 402 is moved between at least two positions. The first position, illustrated in FIG. 4A, enables opening and closing of the anvil assembly 302 via rotation of the firing rod 402 about longitudinal axis K-K; the second position, illustrated in FIG. 4B, enables advancement of pushers 324 to push fasteners 322 through tissue.

In FIG. 4A the firing rod 402 is shown in the first position. The distal shaft 406 of the firing rod 402 includes a cam member 408, which is shown as a dual cam, disposed thereon. In the first position, the cam member 408 is positioned in a plane perpendicular to the longitudinal axis L-L at the distal end of the anvil assembly 302. During operation, the firing rod 402 is rotated, which causes rotation of the cam member 408. As the cam member 408 is rotated, the proximal end of the anvil assembly 302 is pushed upwards by the perpendicular displacement of the cam member 408 thereby closing the anvil assembly 302 against the cartridge assembly 300 (FIG. 4B).

The anvil assembly 302 is pivotally coupled to the cartridge assembly via tabs 332 which extend downwards therefrom. The tabs 332 fit into corresponding slots (not explicitly shown) to provide a hinge point for the anvil assembly 332 to pivot thereabout. This allows the anvil assembly 302 to pivot with respect to the cartridge assembly 300. As the firing rod 408 is rotated further the anvil assembly 302 reverts to open position via one or more biasing members (e.g., springs) pushing upwards on the opposite side of the tabs 332.

Various types of cams may be used to open and close the anvil assembly 302, such as single cams, or multi-cams. Other cam shapes may also be utilized which have a less aggressive angle utilizing full 360° of rotation allowing the anvil assembly 302 to reach full displacement at a more gradual rate. Angle of rotation of the firing rod 402 varies with the type of cam being used, such as for the cam member 408, the firing rod 402 is rotated 90° in order to actuate the anvil assembly 302. In other words, the cam member 402 allows for maximum displacement of the anvil assembly 302 under 90°. It is also envisioned that the firing rod 402 may be rotated in either direction, clockwise or counterclockwise, to actuate the anvil assembly 302.

While in the first position the firing rod 402 is prevented from longitudinal movement in the distal direction by the proximal end of the cartridge assembly 300 and the cam member 408. The walls of the support channel 310 act as a stop member when the firing rod 402 is moved in the distal direction. Once the firing rod 402 is rotated into second position as shown in FIG. 4B, the firing rod 402 can be advanced distally to push the actuation sled 330 through the staple cartridge 312 since the firing rod 402 is no longer stopped by the distal end of the cartridge assembly. The firing rod 402 is movable through the cam member 408, the interface between an aperture through the cam member 408 and the firing rod 402 being shaped to allow a telescoping movement, but also shaped so that the cam member 408 and firing rod 402 rotate together. For example, the cam member 408 and firing rod 402 have a hexagonal shaped interface as shown in FIGS. 4A and 4B. Other shapes, such as helical, star shaped, splined, oval, slotted, and octagonal, can be used.

During operation of surgical stapler, the firing rod 402 abuts actuation sled 330 and pushes actuation sled 330 through longitudinal slots 326 of staple cartridge 312 to advance cam wedges 328 of sled 330 into sequential contact with pushers 324. Pushers 324 translate vertically along cam wedges 328 within fastener retention slots 320 and urge fasteners 322 from retention slots 320 into staple deforming cavities 304 (FIG. 4) of the anvil assembly 302.

Figure 6:
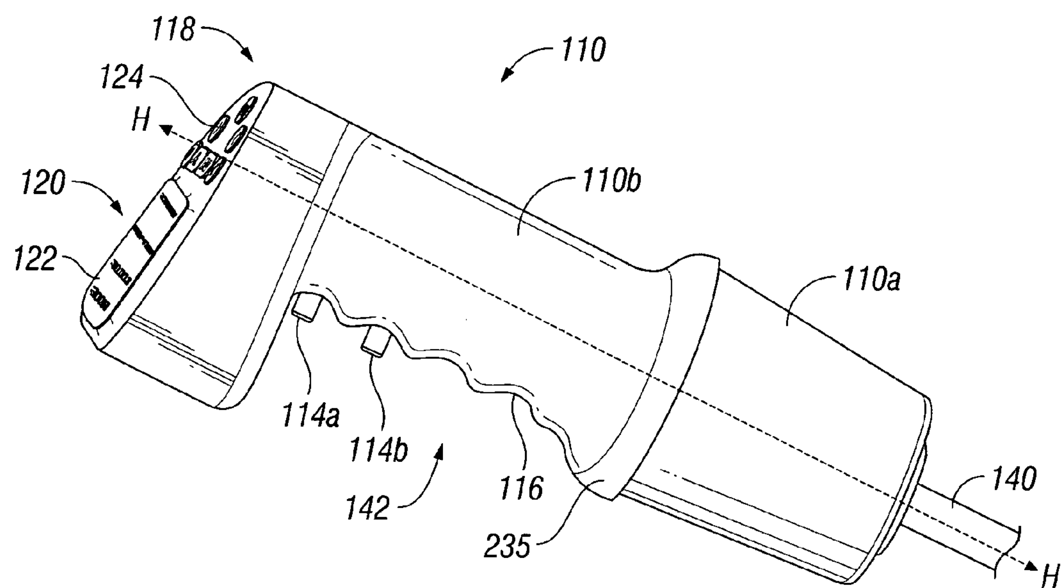
FIG. 6 is an enlarged perspective view of a handle of the powered surgical instrument of FIG. 1.
Figure 7:
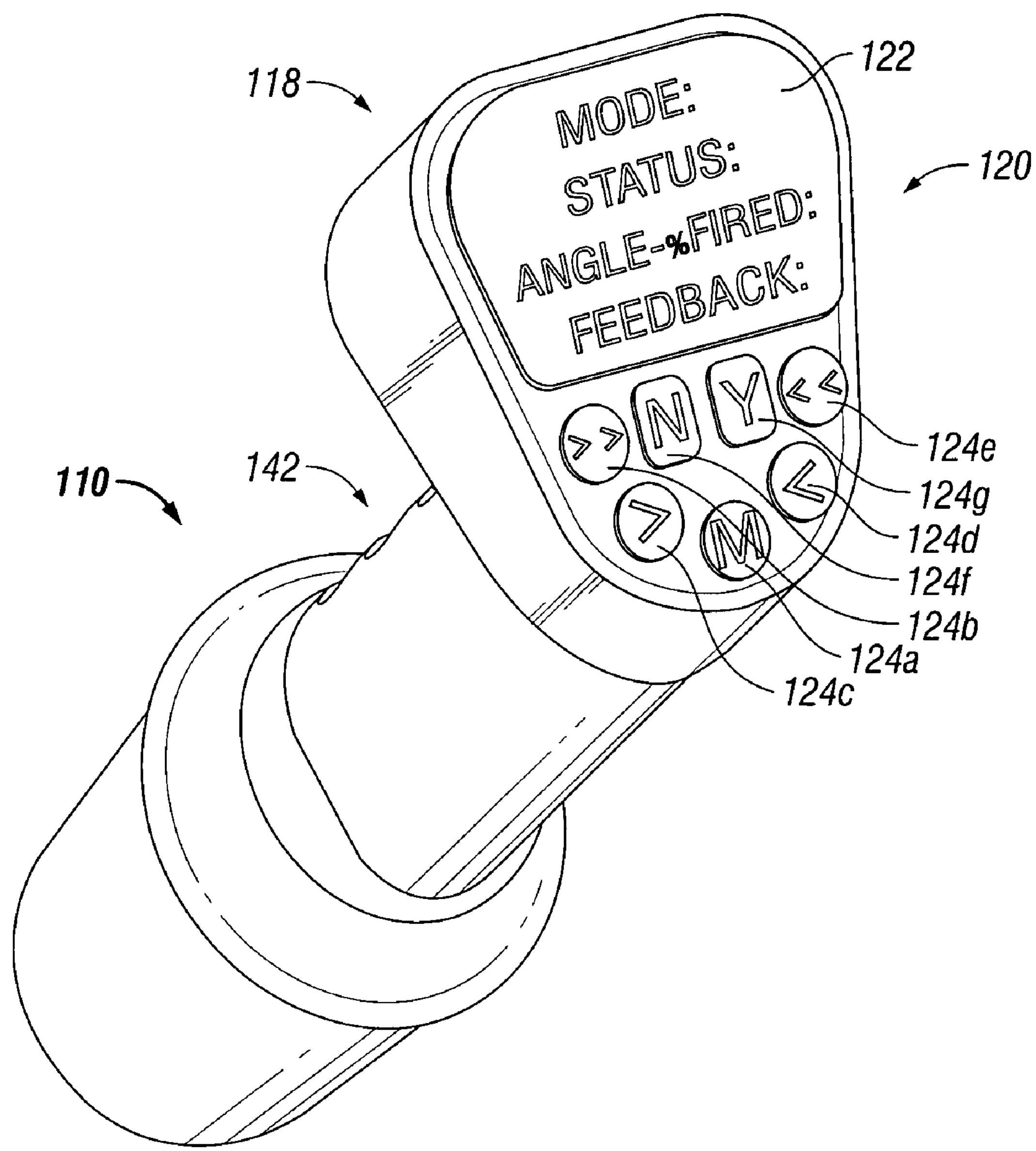
FIG. 7 is an enlarged perspective view of a user interface of the powered surgical instrument of FIG. 1.

With reference to FIGS. 6 and 7, an enlarged view of housing 110 is illustrated according to an embodiment of the present disclosure. In the illustrated embodiment, housing 110 includes a handle portion 110*b* having two buttons 114*a* and 114*b*. Handle portion 110*b*, which defines a handle axis H-H, is shown having indentations 116 that correspond to fingers of a user. Each button 114*a* and 114*b* is shown as being disposed on an indentation 116 to facilitate its depression by a user's finger.

A proximal area 118 of housing 110 includes a user interface 120. In the illustrated embodiment, user interface 120 includes a screen 122 and at least one switch 124 (seven switches 124*a*-124*g* are shown). Screen 122 displays readable information thereon, including status information of powered surgical instrument 100 in an embodiment.

FIG. 7 shows user interface 120 including screen 122 and seven switches 124*a*-124*g*. In the illustrated embodiment, user interface displays the "mode" (e.g., rotation, articulation or actuation), which may be communicated to user interface 120 via shift sensor 224, "status" (e.g., angle of articulation, speed of rotation, or type of actuation) and "feedback," such as whether staples have been fired. Switch 124*a* is shown having an "M," standing for mode, which may be used to position drive gear 200 via shift motor 220 for selecting between rotation, articulation, grasping, clamping and firing. It is also envisioned that switch 124*a* can be used to let a user input different tissue types, and various sizes and lengths of staple cartridges.

Switches 124*b*-124*e* are shown with arrows thereon and may be used for selecting the direction, speed and/or torque at which drive gear 200 is rotated by drive motor 210. It is also envisioned that at least one switch 124 can be used for selecting an emergency mode that overrides various settings. Further, switches 124*f* and 124*g* are illustrated having an "N" and a "Y" thereon. It is envisioned that switches 124*f* and 124*g* may be used for helping a user navigate user interface menus and select various setting of powered surgical instrument 100. The indicia on switches 124*a*-124*g* and their respective functions are not limited by what is shown in the accompanying figures, as deviations therefrom are contemplated and within the scope of the present disclosure. Additionally, and with reference to FIGS. 1 and 6, buttons 114*a* and 114*b* may be used for starting and/or stopping movement of drive motor 210 and/or shift motor 220 and the like.

FIGS. 8-14 illustrate various internal components of powered surgical instrument 100, including a drive gear 200, a drive motor 210 and a shift motor 220. Power is provided via a battery pack 401 (or fuel cell assembly). Other power-supplying means are also contemplated (e.g., electrical transformers coupled to conventional electrical power supplies).

Figure 8:
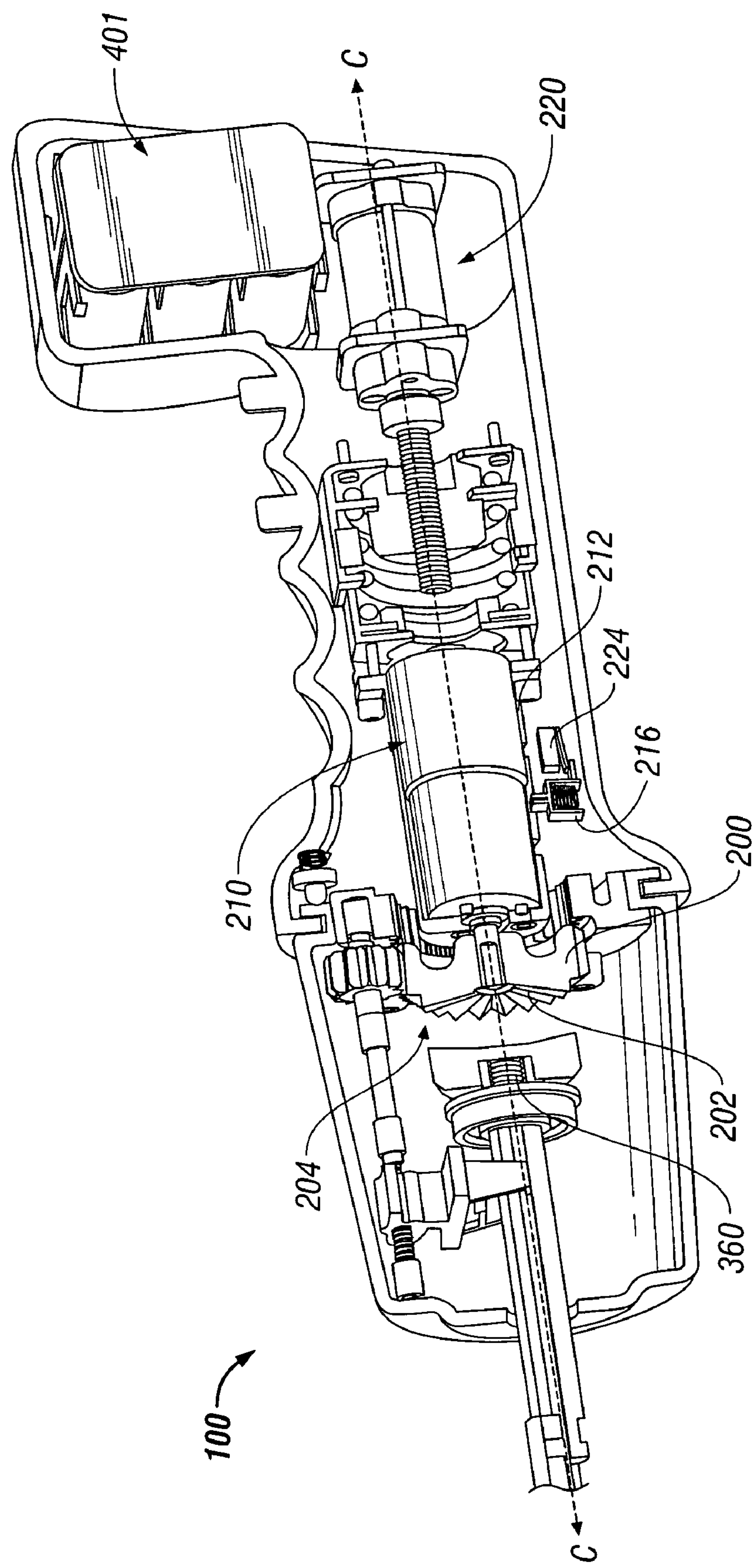
FIG. 8 is a perspective view of internal components of the powered surgical instrument of FIG. 1.

As shown in FIG. 8, the drive gear 200, the drive motor 210 and the battery pack 401 are disposed within the housing 110, specifically a proximal housing portion 110*b*. It is envisioned that these components may also be located within or closer to a distal housing portion 110*a*. The primary or a secondary motor, transmission, and/or the batteries may be disposed in the endoscopic portion 140.

Drive gear 200 is rotatable about a drive gear axis C-C extending therethrough (FIG. 8) and is selectively movable along drive gear axis C-C. Drive motor 210 is disposed in mechanical cooperation with drive gear 200 and is configured to rotate drive gear 200 about drive gear axis C-C. Shift motor 220 is disposed in mechanical cooperation via the drive motor 210 with drive gear 200 and is configured to translate drive gear 200 axially along drive gear axis C-C.

Shift motor 220 is configured to selectively move drive gear 200 between a plurality of positions. In embodiments, the drive gear 200 is moved between three positions. The first position, illustrated in FIGS. 9 and 10, enables rotation of end effector 160; the second position, illustrated in FIG. 11, enables articulation of end effector 160; and the third position, illustrated in FIGS. 13-14, enables actuation of powered surgical instrument 100.

Figure 9:
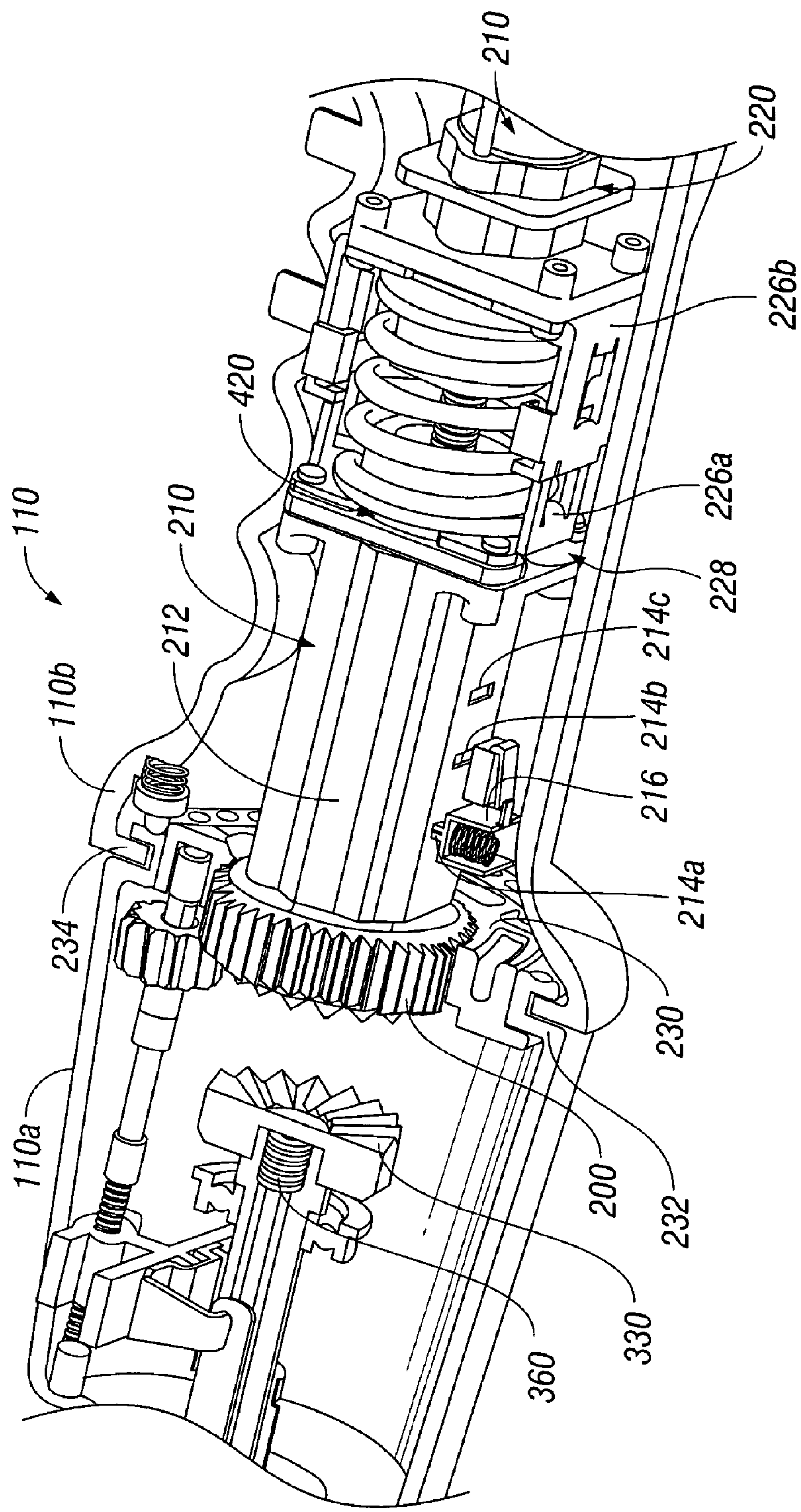
FIGS. 9 and 10 are perspective views of the internal components of the powered surgical instrument of FIG. 1 disposed in a first position, powered rotation.

In the embodiment illustrated in FIG. 9, shift motor 220 is shown including a two-part housing 226. Each part 226*a* and 226*b* of two-part housing 226 are slidably engaged with each other. It is envisioned that part 226*a* is rigidly secured to a drive motor casing 212, while part 226*b* is affixed to drive motor 210 and is translatable within housing 110. Additionally, a wiring slot 228 may be included to allow for wires (not explicitly shown) to pass from transducer 420 towards user interface 120, for example.

Figure 10:
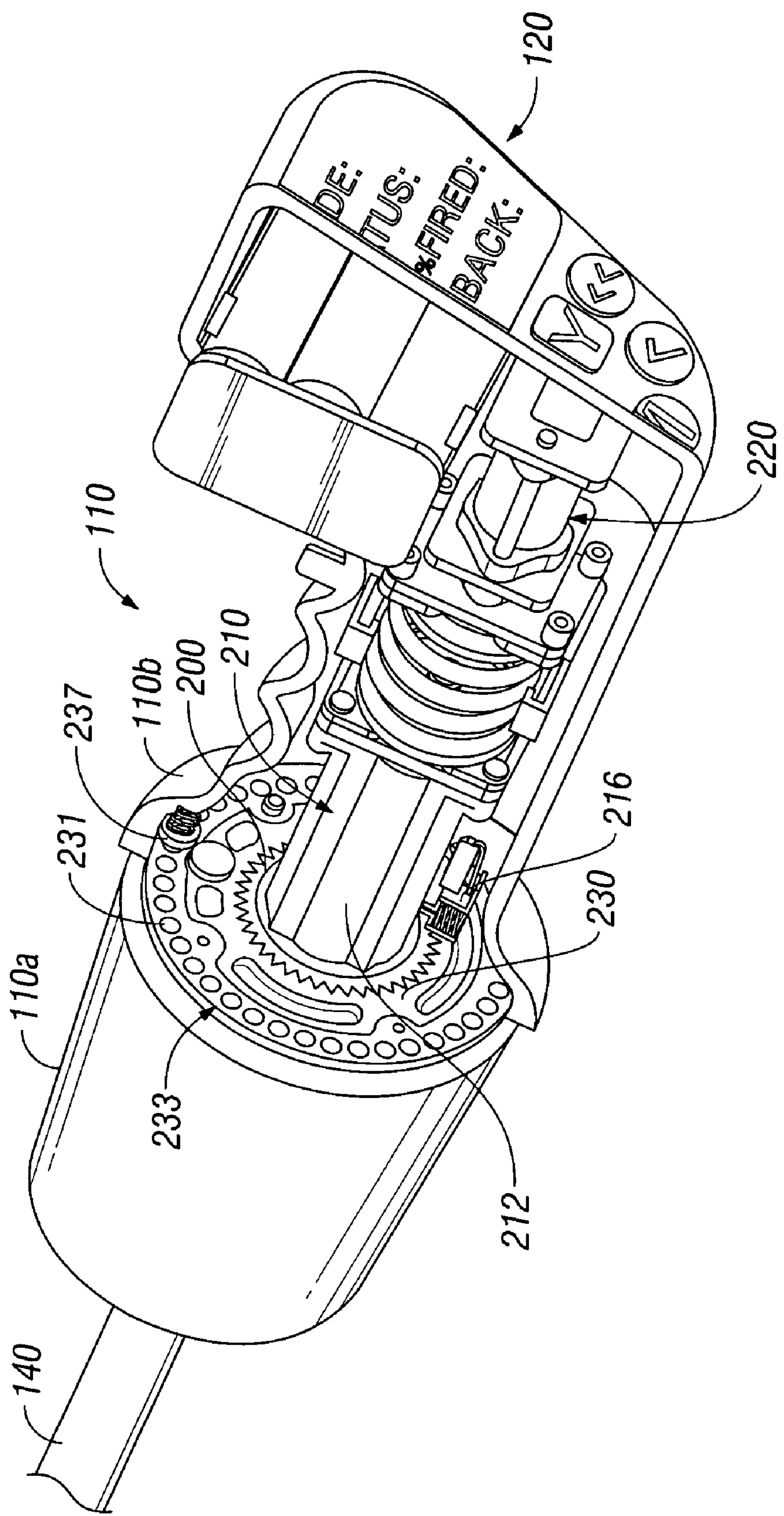
Figure 11:
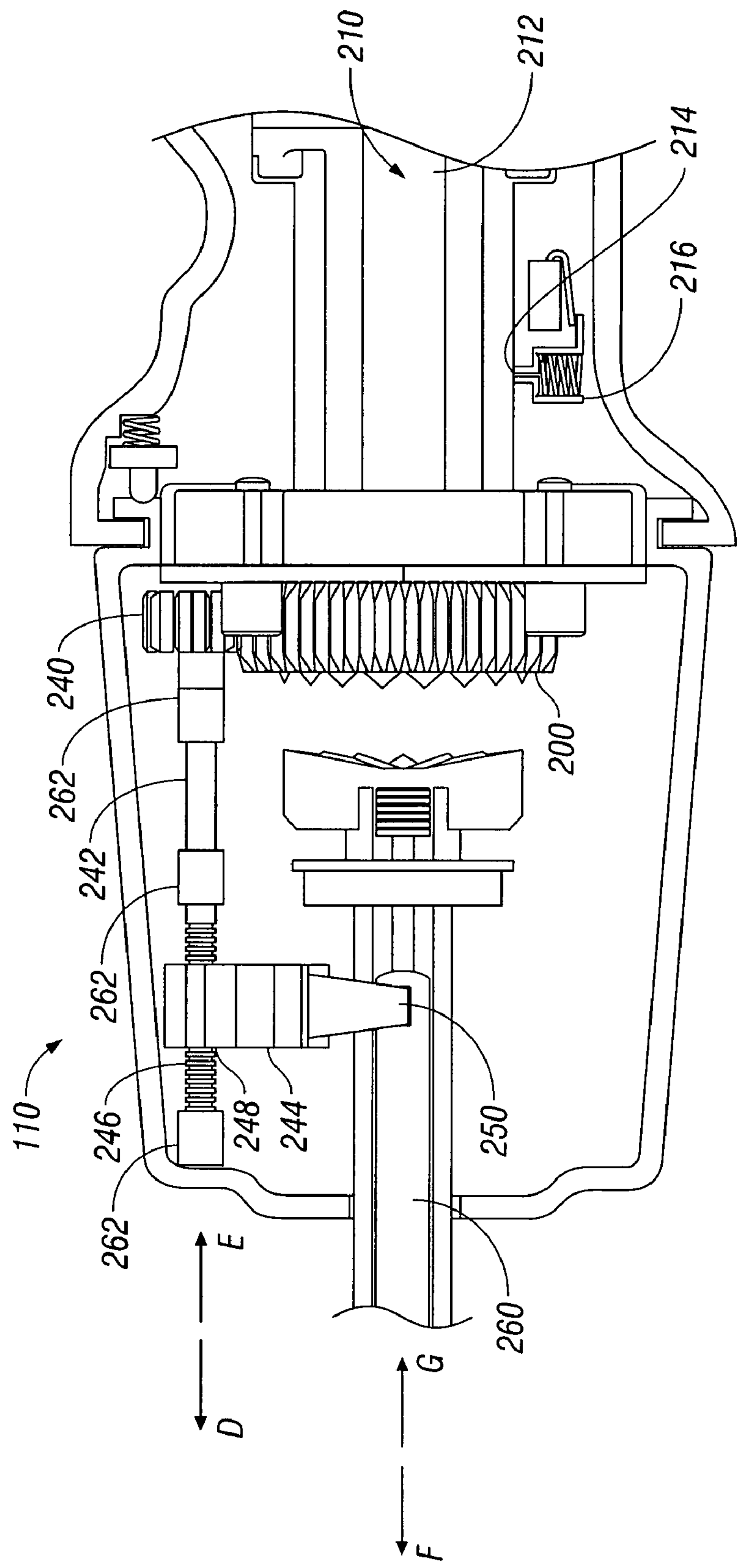
FIG. 11 is a side view of the internal components of the powered surgical instrument of FIG. 1 disposed in a second position, powered articulation.
Figure 13:
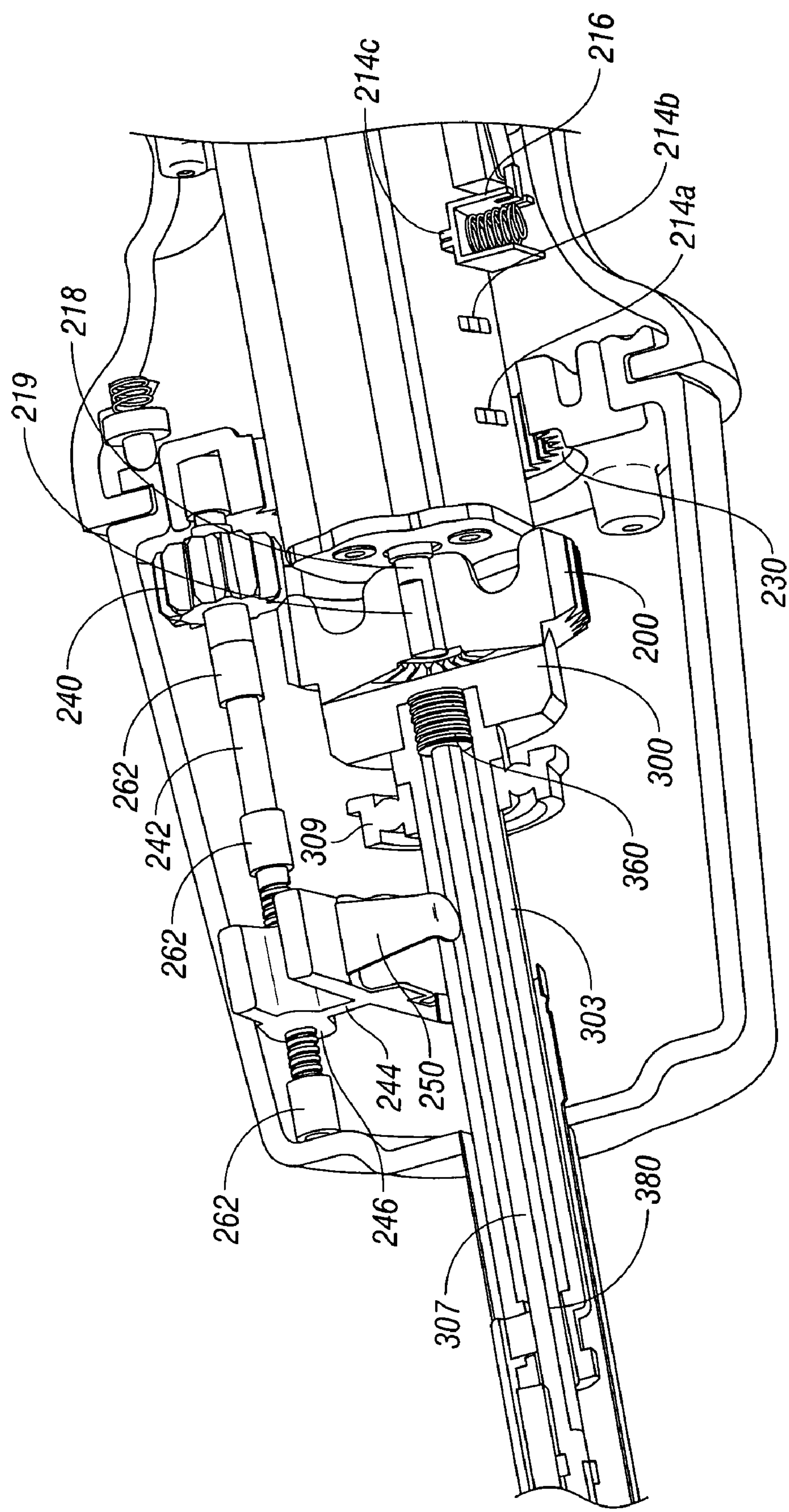
FIGS. 13-14 are perspective view of the internal components of the powered surgical instrument of FIG. 1 disposed in a third position, fire, clamp, grasp, retraction.
Figure 14:
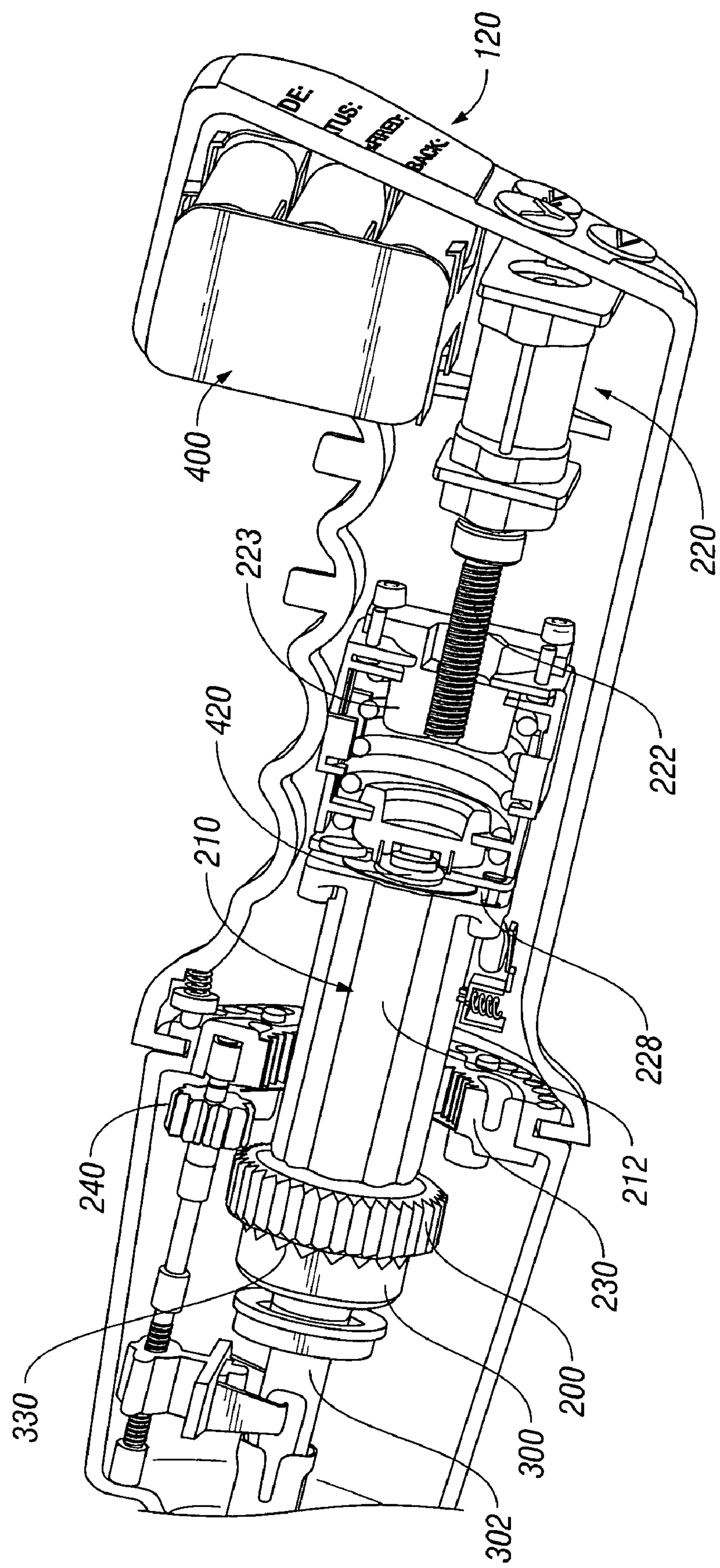

A cut away of the drive motor casing 212, at least partially surrounding drive motor 210, is illustrated in FIGS. 8-11. Drive motor casing 212 includes slots 214*a*, 214*b* and 214*c* therein. Each slot 214 is configured to mate with a position lock 216 to maintain drive gear 210 in a desired position. In FIG. 9, position lock 216 is shown mated with slot 214*a*-corresponding to drive gear 200 being in its first position. In FIG. 11, position lock 216 is shown mated with slot 214*b*—corresponding to drive gear 200 being in its second position. FIGS. 13 and 14 illustrate position lock 216 mated with slot 214*c*—corresponding to drive gear 200 being in its third position. Position lock 216, in the illustrated embodiments, is spring-loaded and biased against the drive motor casing 212, which maintains drive motor 210 is a desired position.

In the illustrated embodiments, shift motor 220 is located proximally of drive motor 210 and is configured to translate drive motor 210 along drive gear axis C-C between its first, second and third positions. Referring to FIG. 14, shift motor 220 is illustrated being driven by a shift screw 222 in conjunction with an internally-threaded screw housing 223, in accordance with a disclosed embodiment. It is further disclosed that a shift sensor 224 (See FIG. 8) (e.g., micro switch or optical/ferromagnetic proximity sensor activate by position lock 216), disposed adjacent position lock 216, electrically communicates with at least one switch 124 to start or stop shift motor 220 and/or provides feedback relating to the position of drive motor 210 (e.g., position of drive motor 210, such as "rotation," is displayed on screen 122 of user interface 120).

With reference to FIGS. 9 and 10, the first position of drive gear 200 is illustrated. Ring gear 230 is disposed within housing 110, wherein rotation of ring gear 230 causes rotation of endoscopic portion 140, end effector 160 and a distal housing portion 110*a*. Distal housing portion 110*a* is disposed distally of a proximal housing portion 110*b*. The housing portion 110*a* includes a guide channel 232 which is peripherally disposed therein and is configured to interface with a corresponding flange 234 which is peripherally disposed within the proximal housing portion 110*b*. In particular, the flange 234 is configured to slidably rotate within the guide channel 232 thereby allow for rotation of the housing portion 110*a* with respect to proximal housing portion 110*b*. In an embodiment, ring gear 230 is rigidly secured within distal housing portion 110*a* and is matingly engagable with drive gear 200. Thus, rotation of drive gear 200 causes rotation of the ring gear 230 and the housing portion 110*a* along with the end effector 160 about the longitudinal axis B-B.

In FIG. 6, a lip 235 is shown which isolates a user's hand from rotatable distal housing portion 110*a*. It is envisioned that a plurality of washers or ball-bearings (possibly made from synthetic resinous fluorine-containing polymers sold under the trademark TEFLON®) is disposed between distal housing portion 110*a* and proximal housing portion 110*b* to reduce the rotational friction therebetween.

With continued reference to the embodiment illustrated in FIG. 10, a plurality of detents 231 is disposed around a surface 233 of distal housing portion 110*a*. A tab 237 is shown disposed on proximal housing portion 110*b*. In a disclosed embodiment, tab 237 is distally biased (e.g., via tab spring 239) and in mechanical cooperation with at least one of plurality of detents 231. The combination of detents 231 and tab 237 helps secure distal housing portion 110*a* in a rotational position with respect to proximal housing portion 110*b*.

In FIG. 11, drive gear 200 is illustrated in its second position, as position lock 216 is aligned with slot 214*b*. Here, drive gear 200 is matingly engaged with an articulation gear 240, which is disposed at least partially within housing 110. Rotation of articulation gear 240 causes end effector 160 to move from its first position, where longitudinal axis B-B is substantially aligned with longitudinal axis A-A, towards its second position, wherein longitudinal axis B-B is disposed at an angle to longitudinal axis A-A.

In the illustrated embodiments and with specific reference to FIGS. 11 and 12, articulation of end effector 160 is affected by an articulation gear 240, an articulation screw 242, an articulation linkage 244 and at least one articulation rod 260. More specifically, articulation gear 240 is rigidly mounted to articulation screw 242, such that as articulation gear 240 is rotated by rotation of drive gear 200 while in its second position, articulation screw 242 also rotates. A plurality of bearings 262 is illustrated at various locations on articulation screw 242 to facilitate the retaining and aligning of articulation screw drive 242 as well as reducing the friction between articulation screw 242 and housing 110, for example.

With continued reference to FIG. 11, articulation screw 242 includes a threaded portion 246, which extends through an internally-threaded portion 248 of articulation linkage 244. This relationship between articulation screw 242 and articulation linkage 244 causes articulation linkage 244 to move distally and/or proximally (in the directions of arrows F and G) along threaded portion 246 of articulation screw 242 upon rotation of articulation screw 242. For example, as articulation screw 242 rotates in a first direction (e.g., clockwise), articulation linkage 244 move proximally, and as articulation screw 242 rotates in a second direction (e.g., counter-clockwise), articulation linkage 244 move distally.

At least one articulation arm 250 is shown extending from articulation linkage 244. In an embodiment, articulation arm 250 is rigidly connected to articulation rod 260 and it is envisioned that more than one articulation arm 250 is connectable to more than one articulation rod 260. As articulation linkage 244 is translated distally and/or proximally in response to rotation of articulation gear 240, articulation rod(s) 260 is also translated distally and/or proximally (in the directions of arrows F and G, along longitudinal axis A-A) in response thereto. Any combinations of limits switches, proximity sensors (e.g., optical and/or ferromagnetic), linear variable displacement transducers and shaft encoders (disposed within housing 110, for instance) may be utilized to control and/or record the location of articulation linkage 244 and/or articulation angle of end effector 160 and/or position of an actuation rod 306 as discussed below with reference to FIGS. 13 and 14.

Figure 12A:
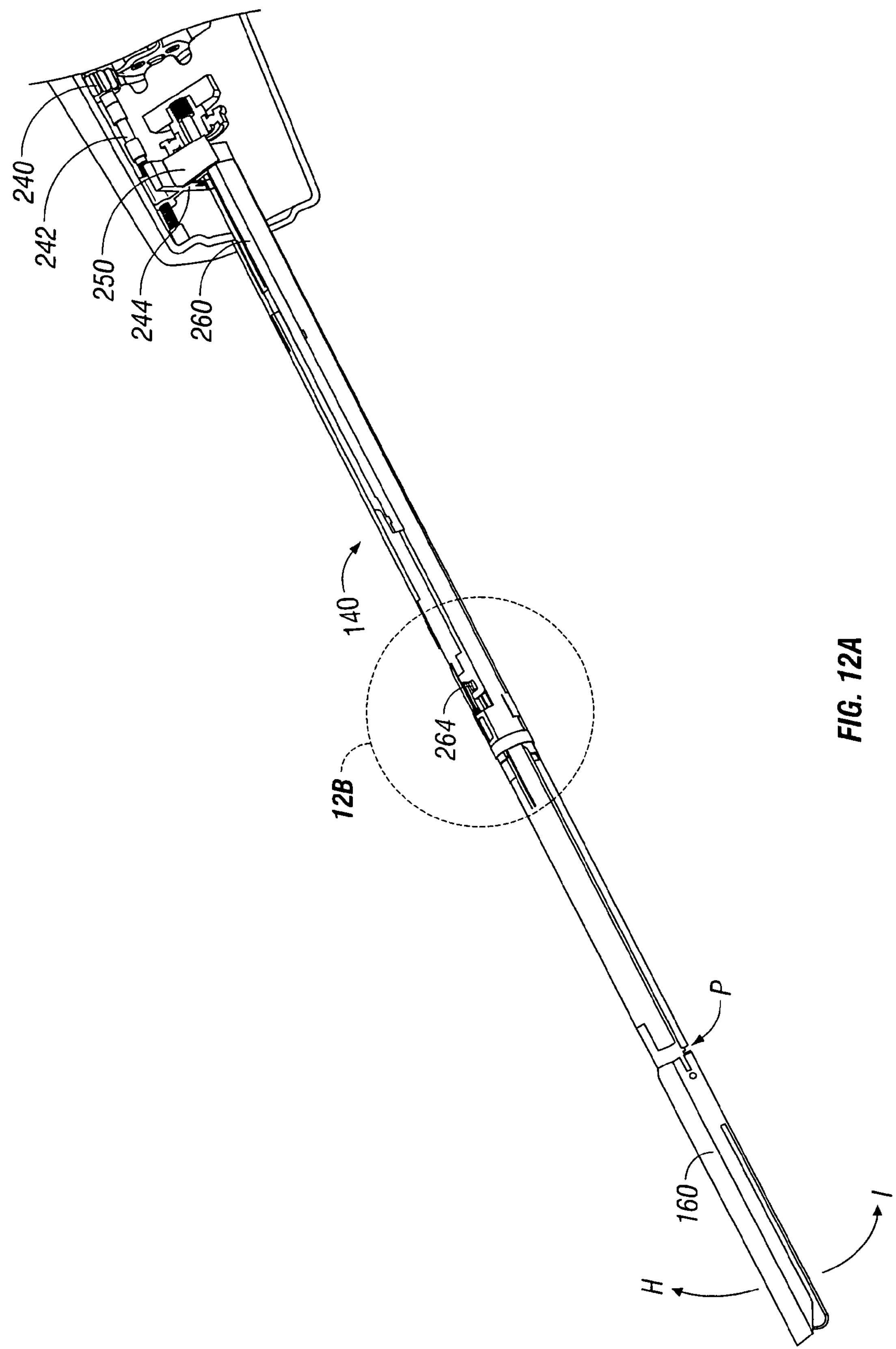
FIG. 12A is a perspective view including an endoscopic portion of the powered surgical instrument of FIG. 1 according to an embodiment of the present disclosure.
Figure 12B:
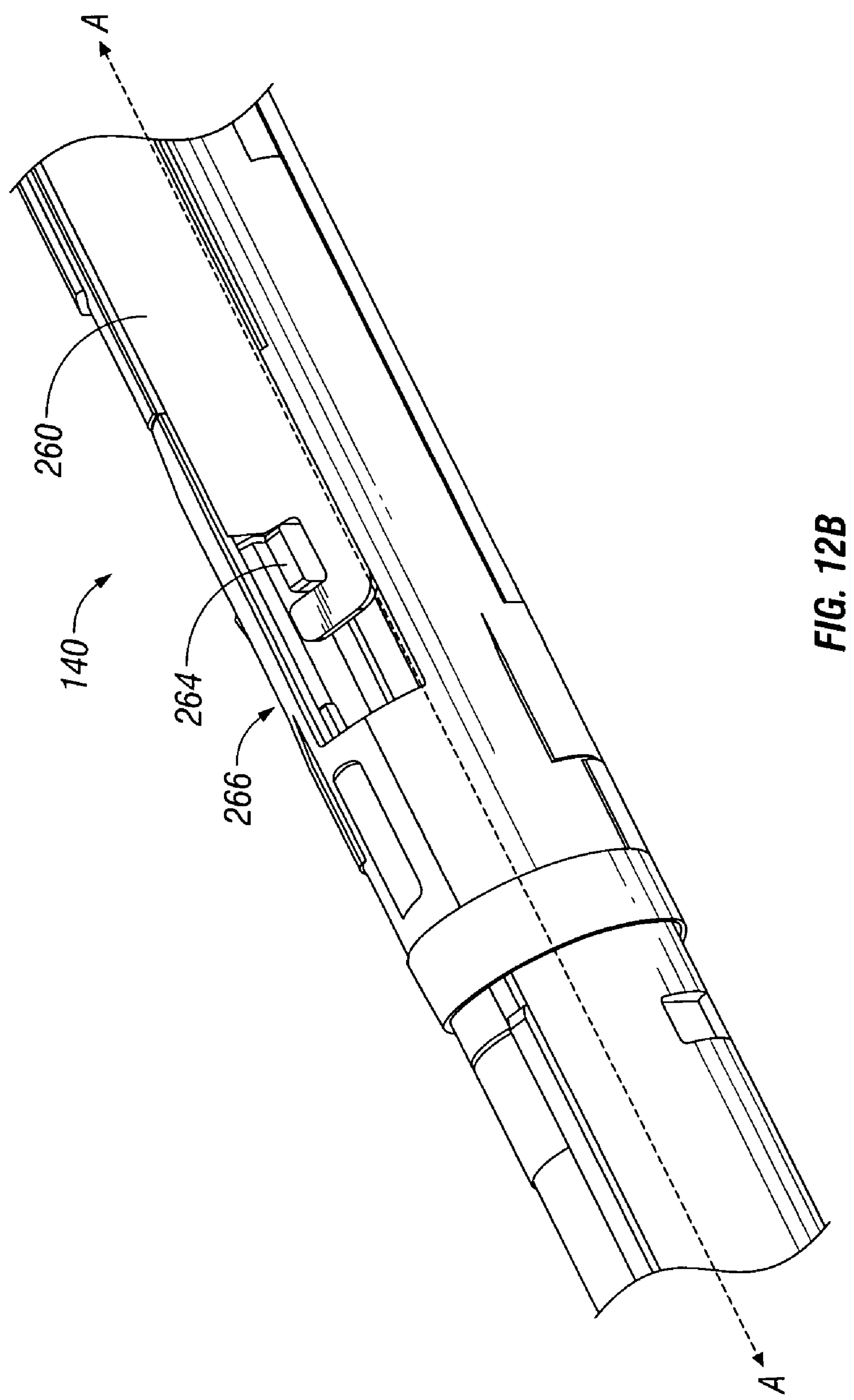
FIG. 12B is an enlarged perspective view of the portion of the powered surgical instrument indicated in FIG. 12A.

With reference to FIGS. 12A and 12B, articulation rod 260 is shown extending through at least a portion of endoscopic portion 140 and in mechanical cooperation with a linkage rod 264. Thus, linkage rod 264 similarly moves along longitudinal axis A-A upon rotation of articulation gear 240. A distal portion 266 of linkage rod 264 is in mechanical cooperation with end effector 160, such that proximal and distal movement of linkage rod 264 causes end effector 160 to move from its first position towards its second position about pivot P. More specifically, and for illustrative purposes, as linkage rod 264 moves distally, end effector 160 is articulated in the direction of arrow H and as linkage rod 264 is translated proximally, end effector 160 is articulated in the direction of arrow I. It is also envisioned that a portion of articulation rod 260 is in mechanical cooperation with end effector 160 to affect articulation thereof. Further details of providing articulation to end effector 160 are described in detail in commonly-owned U.S. Pat. No. 6,953,139 to Milliman et al., the contents of which are hereby incorporated by reference in their entirety.

With reference to FIGS. 13 and 14, drive gear 200 is illustrated in its third position, with position lock 216 aligned with slot 214*c*. The drive gear 200 is matingly engaged with an actuator gear 300, which is disposed at least partially within housing 110. More specifically, a set of teeth 202 disposed on a face 204 (FIG. 8) of drive gear 200 matingly engage actuator gear 300 to provide at least one of grasping tissue, clamping tissue, firing of end effector 160 (e.g., stapling and cutting) and retracting elements to their original position.

With reference to FIG. 13, a drive motor shaft 218 is shown extending from drive motor 210 and being connected to drive gear 220. A fastener (not explicitly shown in this embodiment) may be used to retain drive gear 220 on drive motor shaft 218. Drive motor shaft 218 is rotated by drive motor 210, thus resulting in rotation of drive gear 220. Drive motor shaft 218 is shown having a flat portion 219 (more than one flat portions 219 may be included), which allows "play" or "rotational float" between drive gear 220 and drive motor shaft 218 to facilitate tooth alignment and to help enable drive gear 220 to shift between positions. FIG. 13 also illustrates a bearing 309 disposed within housing 110 and at least partially surrounding drive tube 303. Bearing 309 facilitates rotation of drive tube 303 and aligns drive tube 303 through endoscopic portion 140.

In FIG. 14, a transducer 420 is shown adjacent drive motor 210 and shift motor 220. Transducer 420 (e.g., a force or pressure transducer) may measure and/or control the force required for the desired pressure on actuator gear 330. Transducer 420 may be in communication with portions of user interface 120, which may provide feedback to a user.

With reference to FIGS. 13 and 14, a drive tube 303 and an actuation rod 307 are also included. Drive tube 303 is rigidly attached to actuator gear 300. In an embodiment of the disclosure, actuation rod 307 extends at least to distal portion 142 of endoscopic portion 140 and is mechanically coupled to the firing rod 402. In response to rotation of drive gear 200, actuator gear 300 and drive tube 303 also rotate. As drive tube 303 rotates, the actuation rod 307 is driven forward by the threaded bung 360. Actuation rod 307 is prevented from rotation by flat/non-round features 380 which are mated to the tube housing cross section 266. When unlocked, rotation of actuation rod 307 rotates the firing rod 402 which closes the anvil assembly 302 of end effector 160 to grasp or clamp tissue held therebetween. Further details of firing end effector 160 (or actuation) are described in detail in commonly-owned U.S. Pat. No. 6,953,139 to Milliman et al., the entire contents of which are hereby incorporated by reference herein.

The firing rod 402 can be advanced distally to advance the actuation sled 330 either manually or automatically (e.g., via motorized mechanisms). An example of a powered stapler configured for advancing a firing rod to push fasteners through tissue is illustrated in a commonly-owned U.S. patent application entitled "Powered Surgical Stapling Device" by Marczyk, U.S. application Ser. No. 11/724,744, filed Mar. 15, 2007, the disclosure of which is hereby incorporated by reference herein in its entirety.

Figure 15A:
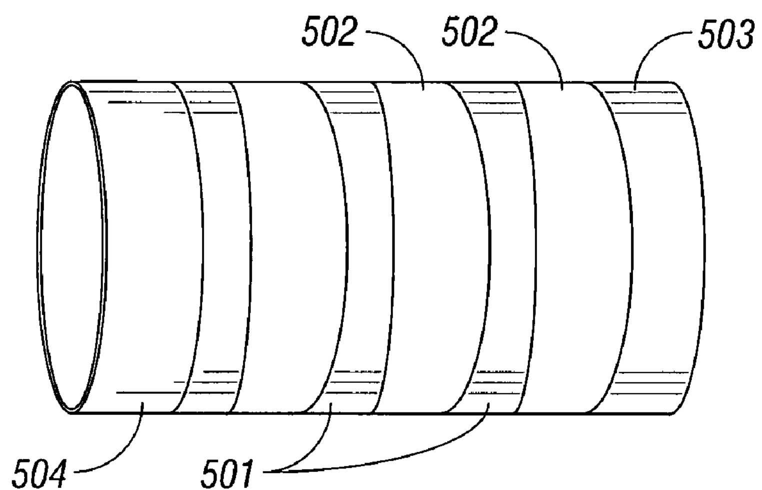
FIGS. 15A-B are perspective views of articulating shaft of the distal portion of the powered surgical instrument of FIG. 1.
Figure 15B:
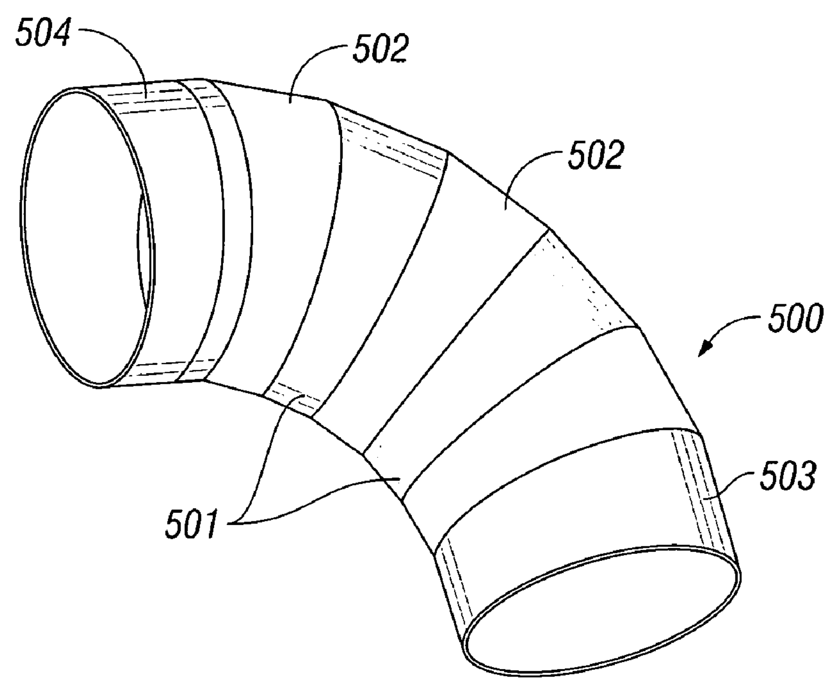

As discussed above, the firing rod 402 is disposed within the endoscopic portion 140 and the distal portion 142. Therefore, in embodiments where the firing rod 402 is formed from a flexible material it is desirable to provide flexible endoscopic portion 140 and distal portion 142. As shown in FIGS. 15A-B, the endoscopic and distal portions 140, 142 are shown as a flexible shaft 500. The flexible shaft 500 includes a plurality of interconnected angled outer tubes 501 and 502. FIG. 15A shows the flexible shaft in a non-articulated formation and FIG. 15B shows the flexible shaft 500 in full articulation formation. When the flexible shaft 500 is straight, narrow sections of the tubes 501 alternate with the wide sections of the tubes 502 as shown in FIG. 15A. When the flexible shaft 500 is fully articulated, the short sides and the wide sides of the tubes 501 and 502 are aligned as shown in FIG. 15B.

The flexible shaft 500 also includes a proximal drive end cap 503 which is in mechanical cooperation with the drive gear 200 and a distal end cap 504 which is in communication with another component of the surgical stapler 10 (e.g., the tool assembly 160 or the distal portion 142 depending where the flexible shaft 500 is disposed). The drive end cap 503 has only one angled face and is turned by the drive gear 200. The end cap 504 is fixed from rotation and also has one angled face and includes an internal stop member for mating with the neighboring tube.

The tubes 500 are mated together by a step which is disposed on the edges of inner surfaces of the tubes 500. The tubes 500 also include stop members at 180 degree positions which interface with neighboring tubes to turn against frictional forces. Each of the tubes 501 and 502 are angled by the same amount on corresponding mating faces and include alternative grooves and ribs which interlock the tubes 501 and 502.

Articulation is achieved by rotation of the tubes 501 and 502 either sequentially or independently. The drive end cap 503 is rotated continuously until the flexible shaft 500 has attained desired articulation position. As the drive end cap 503 is rotated, each tube is rotated correspondingly until the tube reached 90 degree rotation and then locks with the subsequent tube which then begins rotation of the subsequent tube, etc. Use of the flexible shaft 500 in manual or motor-driven instruments is contemplated. A designated motor, or a motor driving multiple functions of the instrument may be used. One of the positions of the shift motor 220 can engage a ring gear operatively connected to proximal drive end cap 503 so that drive gear 200 can drive rotation of the proximal drive end cap 503.

In further embodiments, the endoscopic portion 140 is configured to interchangeably mate with a variety of surgical end effectors including, but not limited to, circular surgical staplers, linear surgical staplers, and others. The endoscopic portion 140 may be relatively rigid, flexible (such as the shaft shown in FIGS. 15A and 15B) and/or articulating.

In certain embodiments, a digital control module (DCM) is desirably included in the housing 110 and can be configured and arranged to control or help control the operation of shift motor 220 and/or drive motor 210 to respond to the monitored information. Pulse modulation, which may include an electronic clutch, may be used in controlling the output. For example, the DCM can regulate the voltage or pulse modulate the voltage to adjust the power and/or torque output to prevent system damage or optimize energy usage. An electric braking circuit may be used for controlling the drive motor 210 and/or shift motor 220, which uses the existing back electromotive force (EMF) of rotating drive motor 210 to counteract and substantially reduce the momentum of drive gear 200. The electric braking circuit may improve the control of drive motor 210 and/or shift motor 220 for stopping accuracy and/or shift location of powered surgical instrument 100. Sensors for monitoring components of powered surgical instrument 100 and to help prevent overloading of powered surgical instrument 100 may include thermal-type sensors, such as thermal sensors, thermistors, thermopiles, thermo-couples and/or thermal infrared imaging and provide feedback to the DCM. The DCM may control the components of powered surgical instrument 100 in the event that limits are reached or approached and such control can include cutting off the power from the battery pack 400, temporarily interrupting the power or going into a pause mode, pulse modulation to limit the energy used, and the DCM can monitor the temperature of components to determine when operation can be resumed. The above uses of the DCM may be used independently of or factored with current, voltage, temperature and/or impedance measurements.

An identification system may also be included to determine and communicate to the DCM various information, including the speed, power, torque, clamping, travel length and strength limitations for operating the particular end effector 160. The DCM may also determine the operational mode and adjust the voltage, clutch spring loading and stop points for travel of the components. More specifically, the identification system may include a component (e.g., a microchip, emitter or transmitter) in end effector 160 that communicates (e.g., wirelessly, via infrared signals, etc.) with the DCM, or a receiver therein. It is also envisioned that a signal may be sent via firing rod, such that the firing rod functions as a conduit for communications between the DCM and end effector 160. The identification system communicates with the DCM information concerning the surgical instrument, such as, for example, the type of end effector attached to the surgical instrument and/or the status of the end effector.

In a disclosed embodiment, at least some of the information monitored by the various sensors in powered surgical instrument 100 may be provided to a video screen or monitoring system in an operating room. For instance, the data may be transmitted to a receiver for the operating room monitoring system from a communication transmitter incorporated in or associated with powered surgical instrument 100, via technology including Blue Tooth, ANT3, KNX, Z Wave, X10, wireless USB, WiFi, IrDa, Nanonet, Tiny OS, ZigBee, radio, UHF and VHF. Such features may facilitate monitoring by the user of powered surgical instrument 100 or other operating room or hospital personnel or remotely located persons.

It will be understood that various modifications may be made to the embodiments disclosed herein. For example, a shorter elongated tubular portion containing more or less coil fasteners may be provided for greater ease of handling during open surgery. Various articulations may be provided along the length of the elongated tubular portion to facilitate positioning of the coil fastener applier within the body. Additionally various configurations of the drive rod and slots or fastener retaining structure may be provided to accommodate various types of rotary fasteners. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:

a housing;

an endoscopic portion extending distally from the housing and defining a first longitudinal axis;

an end effector disposed adjacent a distal portion of the endoscopic portion, the end effector including an anvil assembly and a cartridge assembly, the anvil assembly is pivotally coupled to the cartridge assembly between a first open position spaced from the cartridge assembly and a second position in approximation with the cartridge assembly;

a firing rod defining a second longitudinal axis, and a dual rotary cam member having a pair of opposing camming surfaces rotatable by the firing rod, the cam member being in contact with a proximal end of an inner surface of the anvil assembly and moving the anvil assembly between the first position and the second position, upon rotation of the firing rod about the second longitudinal axis.

2. A surgical instrument according to claim 1, wherein the firing rod includes a proximal shaft member disposed within the end effector and a distal shaft member disposed within the endoscopic portion.

3. A surgical instrument according to claim 2, wherein the proximal shaft member and the distal shaft member are pivotally linked.

4. A surgical instrument according to claim 2, wherein at least one of the proximal shaft member and the distal shaft member is flexible.

5. A surgical instrument according to claim 2, wherein the proximal shaft and the distal shaft include at least one surface feature along the length thereof.

6. A surgical instrument according to claim 5, wherein the at least one surface feature is selected from the group consisting of a non-circular cross-section and a curved shape.

7. A surgical instrument according to claim 1, wherein the end effector defines a third longitudinal axis, the end effector being movable from a first articulation position where the second longitudinal axis is substantially aligned with the first longitudinal axis to at least a second articulation position where the third longitudinal axis is disposed at an angle to the first longitudinal axis.

8. A surgical instrument, comprising:

a housing;

an endoscopic portion extending distally from the housing and defining a first longitudinal axis;

an end effector disposed adjacent a distal portion of the endoscopic portion, the end effector including a first jaw member and a second jaw member, the second jaw member is pivotally coupled to the first jaw member to be movable from a first actuation position to at least one other second actuation position; and a firing rod including a shaft defining a second longitudinal axis, a dual rotary cam member having a pair of opposing camming surfaces rotatable by the firing rod, the cam member being in contact with a proximal end of an inner surface of the second jaw member and moving the second jaw member from the first actuation position to the at least one other second actuation position upon rotation of the firing rod about the second longitudinal axis.

9. A surgical instrument according to claim 8, wherein the firing rod includes a proximal shaft member disposed within the end effector and a distal shaft member disposed within the endoscopic portion.

10. A surgical instrument according to claim 9, wherein the proximal shaft member and the distal shaft member are pivotally linked.

11. A surgical instrument according to claim 9, wherein the proximal shaft and the distal shaft include at least one surface feature along the length thereof.

12. A surgical instrument according to claim 11, wherein the at least one surface feature is selected from the group consisting of a non-circular cross-section and a curved shape.

13. A surgical instrument according to claim 9, wherein the end effector defines a third longitudinal axis, the end effector being movable from a first articulation position where the second longitudinal axis is substantially aligned with the first longitudinal axis to at least a second articulation position where the third longitudinal axis is disposed at an angle to the first longitudinal axis.

14. A tool assembly, comprising:

an end effector disposed adjacent a distal endoscopic portion of the tool assembly and defining a first longitudinal axis, the end effector including an anvil assembly and a cartridge assembly, the anvil assembly is pivotally coupled to the cartridge assembly to be movable from a first actuation position to at least one other second position; and a firing rod defining a second longitudinal axis, and a rotary cam member having a pair of opposing camming surfaces rotatable by the firing rod, the cam member being in contact with a proximal end of an inner surface of the anvil assembly and moving the anvil assembly between the first position and the second position, upon rotation of the firing rod about the second longitudinal axis.

15. A tool assembly according to claim 14, wherein the firing rod includes a proximal shaft member disposed within the end effector and a distal shaft member disposed within the endoscopic portion.

16. A tool assembly according to claim 15, wherein the proximal shaft member and the distal shaft member are pivotally linked.

17. A tool assembly according to claim 15, wherein the proximal shaft and the distal shaft include at least one surface feature along the length thereof.

18. A tool assembly according to claim 17, wherein the at least one surface feature is selected from the group consisting of a non-circular cross-section and a curved shape.

19. A tool assembly according to claim 14, wherein the end effector defines a third longitudinal axis, the end effector being movable from a first articulation position where the second longitudinal axis is substantially aligned with the first longitudinal axis to at least a second articulation position where the third longitudinal axis is disposed at an angle to the first longitudinal axis.

* * * * *